(12) United States Patent
Heath et al.

(10) Patent No.: US 7,744,279 B2
(45) Date of Patent: Jun. 29, 2010

(54) ORIENTATION SENSING APPARATUS FOR RADIATION IMAGING SYSTEM

(75) Inventors: Michael D. Heath, Rochester, NY (US); Yawcheng Lo, Rochester, NY (US); Teresa M. Levy, Webster, NY (US); James Doran, Rochester, NY (US)

(73) Assignee: Carestream Health, Inc., Rochester, NY (US)

(*) Notice: Subject to any disclaimer, the term of this patent is extended or adjusted under 35 U.S.C. 154(b) by 20 days.

(21) Appl. No.: 11/924,715

(22) Filed: Oct. 26, 2007

(65) Prior Publication Data

US 2008/0130837 A1 Jun. 5, 2008

Related U.S. Application Data

(60) Provisional application No. 60/863,976, filed on Nov. 2, 2006.

(51) Int. Cl.
*A61B 6/08* (2006.01)
(52) U.S. Cl. .................. 378/205; 378/196; 378/197; 378/198; 378/206
(58) Field of Classification Search .......... 378/117, 378/196–198, 205, 206
See application file for complete search history.

(56) References Cited

U.S. PATENT DOCUMENTS

| 4,752,948 A | 6/1988 | MacMahon |
| 5,241,578 A | 8/1993 | MacMahon |
| 5,388,143 A | 2/1995 | MacMahon |
| 5,690,107 A * | 11/1997 | Hofmann .................. 600/407 |
| 5,828,722 A | 10/1998 | Ploetz et al. |
| 6,154,522 A | 11/2000 | Cumings |
| 6,435,716 B1 * | 8/2002 | Polkus et al. ............... 378/205 |
| 6,461,040 B1 * | 10/2002 | Mattson et al. ............. 378/205 |
| 2002/0150215 A1 * | 10/2002 | Barnes et al. ............... 378/197 |
| 2004/0113778 A1 * | 6/2004 | Script et al. ............. 340/545.1 |
| 2005/0033510 A1 * | 2/2005 | Kawaguchi et al. ......... 701/209 |
| 2005/0058244 A1 | 3/2005 | Tanaka et al. |
| 2006/0109958 A1 | 5/2006 | Ertel et al. |

FOREIGN PATENT DOCUMENTS

| DE | 196 11 705 B4 | 3/1996 |
| EP | 1 000 582 | 5/2000 |
| EP | 1 163 880 | 12/2001 |
| WO | WO 2007/005683 | 1/2007 |

* cited by examiner

*Primary Examiner*—Hoon Song
*Assistant Examiner*—Mona M Sanei

(57) ABSTRACT

A radiation imaging system includes a radiation head with a radiation source and an adjustable angular orientation. A radiation image detection device has a photostimulable medium that records an image according to radiation emitted from the radiation source. A measurement sensor apparatus, preferably inertial, is coupled sequentially to the photostimulable medium to provide three-dimensional data for determining the angular orientation of the photostimulable medium and to the radiation source for determining its angular orientation. There is at least one indicator responsive to the orientation data from the measurement sensor apparatus for indicating an orientation adjustment of the radiation source is needed in at least one direction.

22 Claims, 25 Drawing Sheets

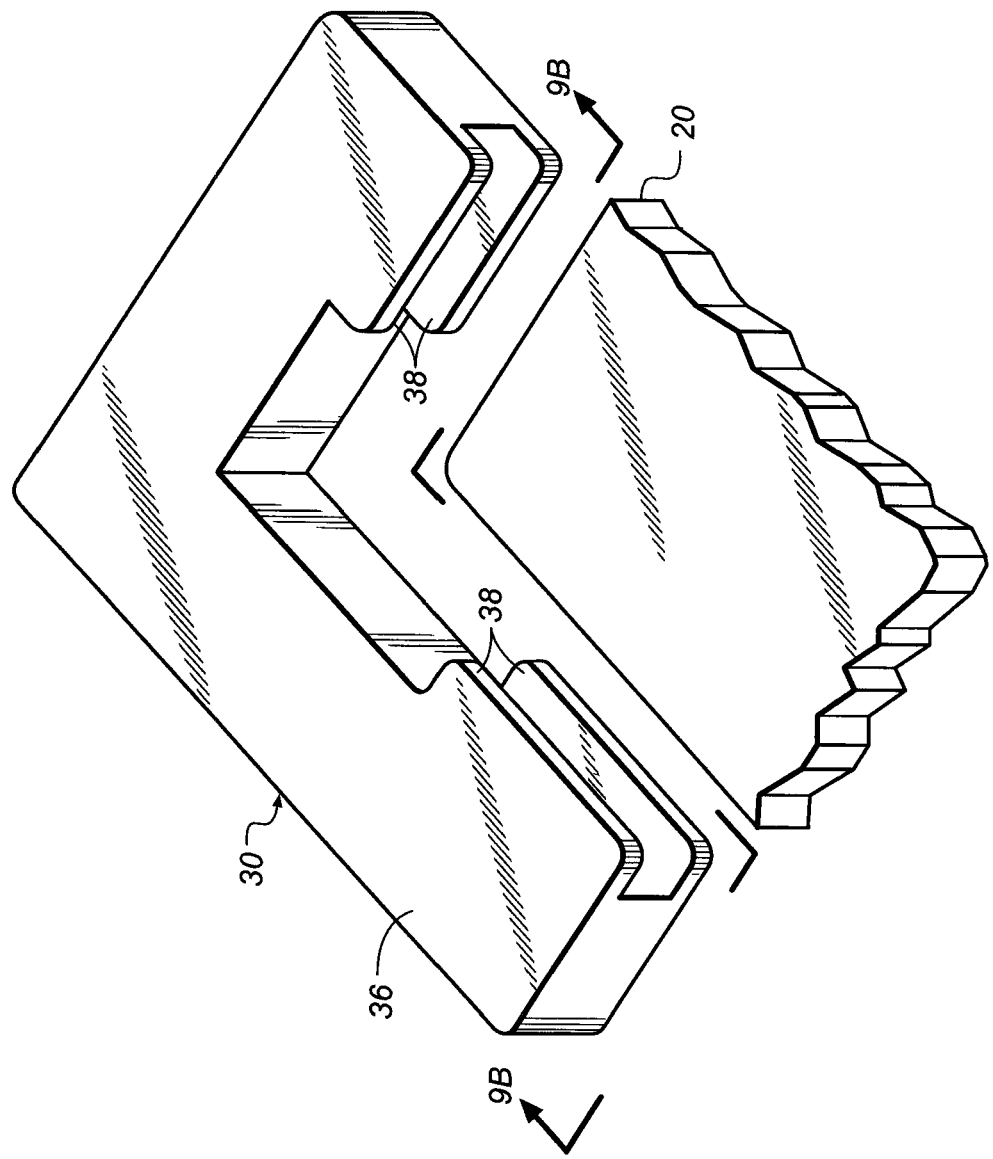

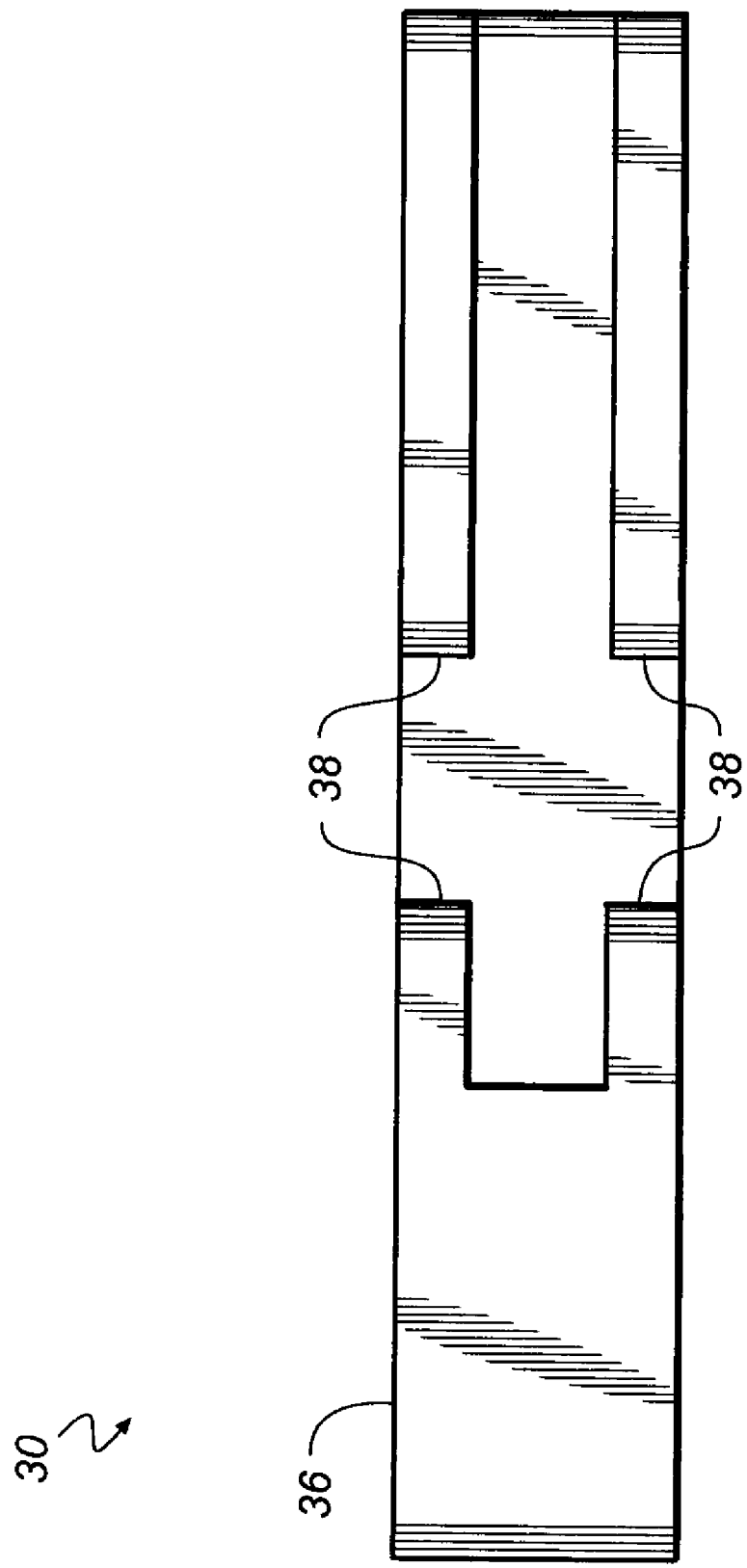

ORIENTATION SENSING APPARATUS FOR RADIATION IMAGING SYSTEM

CROSS-REFERENCE TO RELATED APPLICATION

This application is related to Provisional Application No. 60/863,976 filed Nov. 2, 2006 for Position Sensing Apparatus for Radiation Imaging System.

FIELD OF THE INVENTION

This invention generally relates to a radiation imaging apparatus or system; and more particularly to such an apparatus or system having inertial angular orientation sensing features for facilitating proper alignment of the radiation source relative to an image detection device for recording a radiation image.

BACKGROUND OF THE INVENTION

When an x-ray image is obtained, there is generally an optimal angle between the x-ray source and the usual two-dimensional receiver or image detection device that records the image data. In most cases, the x-ray source preferably provides radiation in a direction that is perpendicular to the surface of the recording medium of the receiver. For this reason, large-scale radiography systems typically mount the radiation head containing the x-ray source at a specific angle relative to the recording medium. Orienting the head and the receiver typically requires a mounting arm of substantial size, extending beyond the full distance between these two components. Unwanted tilt or skew of the receiver is thus prevented by the mounting hardware of the imaging system itself.

With the advent of portable radiation imaging apparatus, such as those used in Intensive Care Unit (ICU) environments, a fixed angular relationship between the radiation source and two-dimensional radiation receiver usually is no longer imposed by the mounting hardware. Instead, a technician or operator is required to aim the radiation source toward the surface of the recording medium, providing as perpendicular an orientation as possible using a visual assessment. In computed radiography (CR) systems, the two-dimensional radiation receiver or image detection device itself is a portable cassette that stores the readable recording medium.

There have been a number of approaches to the problem of providing methods and tools to assist the technician with aiming the radiation source. One approach has been to provide mechanical alignment in a more compact fashion, such as that described in U.S. Pat. No. 4,752,948 entitled "Mobile Radiography Alignment Device" to MacMahon. A platform is provided with a pivotable standard for maintaining alignment between an imaging cassette and radiation source. However, complex mechanical solutions of this type tend to reduce the overall flexibility and portability of these x-ray systems.

Other approaches project a light beam in order to achieve alignment between source and receiver. Examples of this approach include U.S. Pat. No. 5,388,143 entitled "Alignment Method for Radiography and Radiography Apparatus Incorporating Same" and No. 5,241,578 entitled "Optical Grid Alignment System for Portable Radiography and Portable Radiography Apparatus Incorporating Same", both to MacMahon. Similarly, U.S. Pat. No. 6,154,522 entitled "Method, System and Apparatus for Aiming a Device Emitting Radiant Beam" to Cumings describes the use of a reflected laser beam for alignment of the radiation target.

One solution for maintaining a substantially perpendicular relationship between the radiation source and the two-dimensional radiation receiver or image detection device is described in U.S. Patent Application Publication No. 2005/0058244 entitled "Portable Radiation Imaging System and a Radiation Image Detection Device Equipped with an Angular Signal Output Means" by Tanaka et al. This published application discloses an angular sensing device atop or along an edge of the image detection device. The angular sensing device sends a signal to adjust either the tilt angle of the image detection device or the orientation angle of the radiation source in order to maintain a perpendicular relationship of the image detection device to the radiation source. This same approach had previously been used in a number of X-ray products, such as the Siemens Mobilett XP hybrid portable X-ray source, for example, that used built-in tilt sensors.

Similar to the earlier approaches that also used tilt relative to gravity, the solution proposed by Tanaka et al. has limited value for achieving alignment between the image detection device and the radiation source. Measuring tilt with respect to gravity is suitable for one particular case: that is, where the image detection device is intended to be level and where the radiation source is to be perpendicular to the surface of the image detection device. In any other orientation, however, solutions of this type become increasingly less effective as the surface of the image detection device moves away from a perfectly level orientation. There is not enough positioning information with this type of solution for aligning the central ray of the radiation source with the normal to the surface of the image detection device. In the worst-case position, with the image-detection device in a near-vertical or vertical orientation, there is little or no information that can be obtained from tilt sensors as to whether or not the surface of the image detection device is perpendicular to the path of x-rays from the radiation source. Moreover, the particular solution proposed by Tanaka et al. does not assist the technician in making manual adjustments for tilt, but requires a more costly and trouble-prone system having motion control components.

Portable radiation imaging apparatuses allow considerable flexibility for placement of the CR cassette by the technician. The patient need not be in a horizontal position for imaging, but may be at any angle, depending on the type of image that is needed and the ability to move the patient for the x-ray examination. The technician can manually adjust the position of both the cassette and the radiation source independently for each imaging session. Thus, it can be appreciated that an alignment apparatus for obtaining the desired angle between the radiation source and the surface of the image detection device must be able to adapt to whatever orientation is best suited for obtaining the image. Tilt sensing, as has been conventionally applied and as is used in the device of Tanaka et al. and elsewhere, does not provide sufficient information on cassette-to-radiation source orientation, except in the single case where the cassette is level.

Thus, it is apparent that conventional alignment solutions may be workable for specific types of systems and environments; however, considerable room for improvement remains. Portable radiation imaging apparatus must be compact and lightweight, which makes the mechanical alignment approach such as that given in the '948 MacMahon disclosure less than desirable. The constraint to direct line of sight alignment reduces the applicability of reflected light based methods to a limited range of imaging situations. The complex sensor and motion control interaction required by Tanaka et al. would add considerable expense, complexity, weight, and size to existing designs, with limited benefits. Many less expensive portable radiation imaging apparatuses do not have the control logic and motion coordination components that are needed in order to achieve the necessary adjustment. None of these approaches gives the technician the needed information for making a manual adjustment that is in the right direction for correcting misalignment.

Significantly, none of the conventional solutions just described is particularly suitable for retrofit to existing portable radiation imaging apparatus. That is, implementing any of these earlier solutions would be, in practice, prohibitive for all but newly manufactured equipment and would have significant cost impact.

Yet another problem not addressed by many of the conventional solutions relates to the actual working practices of radiologists and technicians. A requirement for perpendicular delivery of radiation, given particular emphasis in Tanaka et al., is not optimal for all types of imaging. Rather, there are some types of diagnostic images for which an oblique (non-perpendicular) incident radiation angle is most desirable. For example, for the standard chest anterior-posterior (AP) view, the recommended central ray angle is oblique from the perpendicular (normal) by approximately 3-5 degrees. Conventional alignment systems, while they provide for normal incidence of the central ray, do not adapt to assist the technician for adjusting to an oblique angle.

Thus, it can be seen that there is a need for an apparatus that enables proper angular alignment of a radiation source relative to an image detection device for recording a radiation image.

SUMMARY OF THE INVENTION

A first embodiment of the invention regards a radiation imaging system including a radiation head with a radiation source and an adjustable angular orientation, and a radiation image detection device including a photostimulable medium that can record an image according to radiation emitted from the radiation source. A measurement sensor apparatus is provided that includes a housing adapted to be sequentially coupled to the detection device and the radiation head, the sensor apparatus providing three-dimensional data for sequentially determining an angular orientation of the detection device and an angular orientation of the radiation head. At least one indicator responsive to angular orientation data from the measurement sensor apparatus is provided to indicate to an operator of the radiation imaging system an angular orientation adjustment to be made in at least one direction for the radiation head.

A second embodiment of the invention regards a measurement sensor apparatus for use in a radiation imaging system of a type including a radiation head and a radiation image detection device. The measurement sensor apparatus includes a housing adapted to be sequentially coupled to the detection device and the radiation head, the sensor apparatus providing three-dimensional data for sequentially determining an angular orientation of the detection device and an angular orientation of the radiation head.

A third embodiment of the invention regards a method for obtaining a radiation image, including steps of coupling a measurement sensor apparatus to a radiation image detection device, wherein the detection device can record an image onto a photostimulable medium according to radiation emitted from a radiation head comprising a radiation source and wherein the measurement sensor apparatus provides three-dimensional data for sequentially determining an angular orientation of the detection device and an angular orientation of the radiation head. The method includes further steps of establishing a first set of three-dimensional data from the measurement sensor apparatus as coupled to the detection device; removing the measurement sensor apparatus from the detection device and coupling the measurement sensor apparatus to the radiation head; establishing a second set of three-dimensional data from the measurement sensor apparatus as coupled to the radiation head; and adjusting the angular orientation of the radiation head according to differences between the first and second sets of three-dimensional data.

It is a feature of the present invention that it provides an angular rate and acceleration sensor that allows the measurement of the relative angular orientation of an X-ray cassette and the radiation source.

It is an advantage of the present invention that it provides data that allows an technician to make accurate alignment adjustments of the radiation head relative to the orientation of a photostimulable medium, such as would be included in a CR cassette.

It is a further advantage of the present invention that it allows a number of configurations for position sensing.

It is a further advantage of the present invention that it allows a technician to know in which direction adjustment is necessary for alignment. The apparatus of the present invention would allow a technician to adjust not only to perpendicular angle of the radiation head relative to the surface of the medium, but would also allow setup of the incident radiation at an oblique angle.

These and other objects, features, and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

FIG. 9A is a perspective view showing how the housing of the sensor can be fitted onto the cassette;

FIG. 9B is a side view of the sensor taken along line 9B-9B of FIG. 9A;

DETAILED DESCRIPTION OF THE INVENTION

The present description is directed in particular to elements forming part of, or cooperating more directly with, an apparatus, system or method in accordance with the invention. It is to be understood that elements not specifically shown or described may take various forms well known to those skilled in the art.

Unlike the limited tilt sensing approaches that have been used in a variety of earlier radiation imaging systems, the apparatus and method of the present invention use three-axis, preferably inertial, measurement components and techniques for obtaining object orientation data that helps to align at the proper angle a radiation source and a two dimensional radiation image detection device. Embodiments of the present invention enable the technician to position the two-dimensional radiation image detection device, also referred to in this description as a computed radiography (CR) cassette, at a favorable angle for the patient, whether in a vertical, oblique, or horizontal position. The technician can then adjust the angle of the radiation head suitably for imaging, using information that is provided from sensors coupled to the cassette and x-ray head, where this information indicates the needed direction of adjustment for alignment correction.

Figure 1:
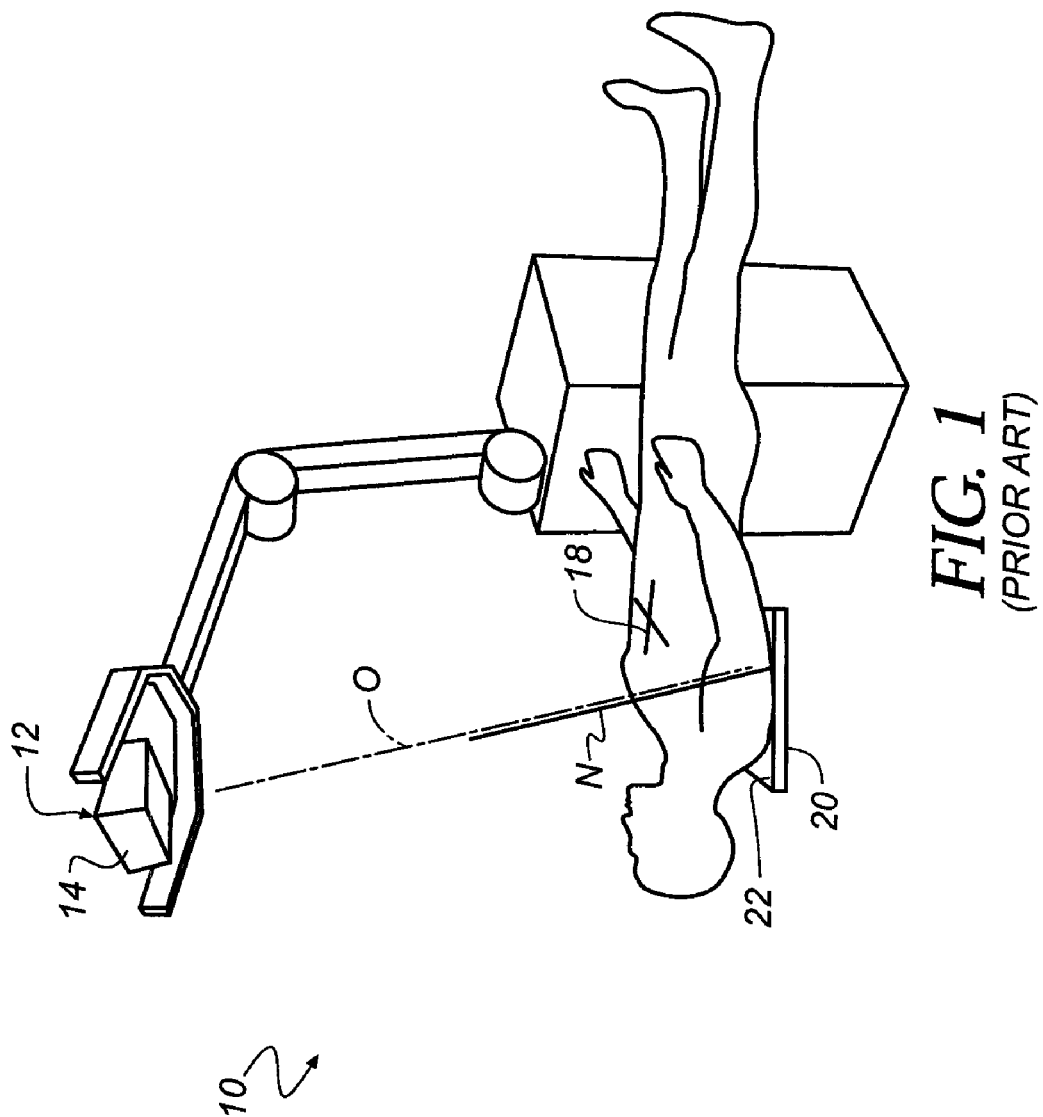
FIG. 1 is a perspective view of a portable radiation imaging apparatus, showing key components and physical relationships.

In order to more fully understand the invention in its various embodiments and the improvements afforded by the present invention, it is first useful to review a number of key problems that must be addressed by an alignment solution. FIG. 1 shows a known type of portable radiation imaging apparatus or system 10 comprising a radiation head 12 that houses an X-ray radiation source 14. Radiation head 12 directs x-ray radiation toward the patient along a central axis O. Radiation head 12 has an adjustable position and angular orientation, thus allowing adjustment of central axis O to suit the requirements of an imaging session. The patient can be in a horizontal position, as shown in the example of FIG. 1, or can be at an oblique or even vertical angle, depending on the type of image that must be obtained. A cassette 20, which serves as the two-dimensional radiation image detection device, has a photostimulable medium that records an image according to the radiation emitted from radiation source 14. For most image types, it is best that central axis O be at least substantially perpendicular to the surface of the medium within cassette 20, that is, aligned with the normal N to the surface of cassette 20. However, as already noted in this specification, there can be situations where an oblique (non-normal) angle is preferred. A target 18, typically provided by a projected beam of visible light, appears on the patient and helps the technician to aim radiation head 12 to a suitable location. Since radiation head 12 has both an adjustable position and orientation, target 18 may be aimed at a suitable location, given many combinations of position and orientation of radiation source 14. Some combinations of positions and orientations of radiation head 12 may be suitable for an examination, while others may not.

Figure 2:
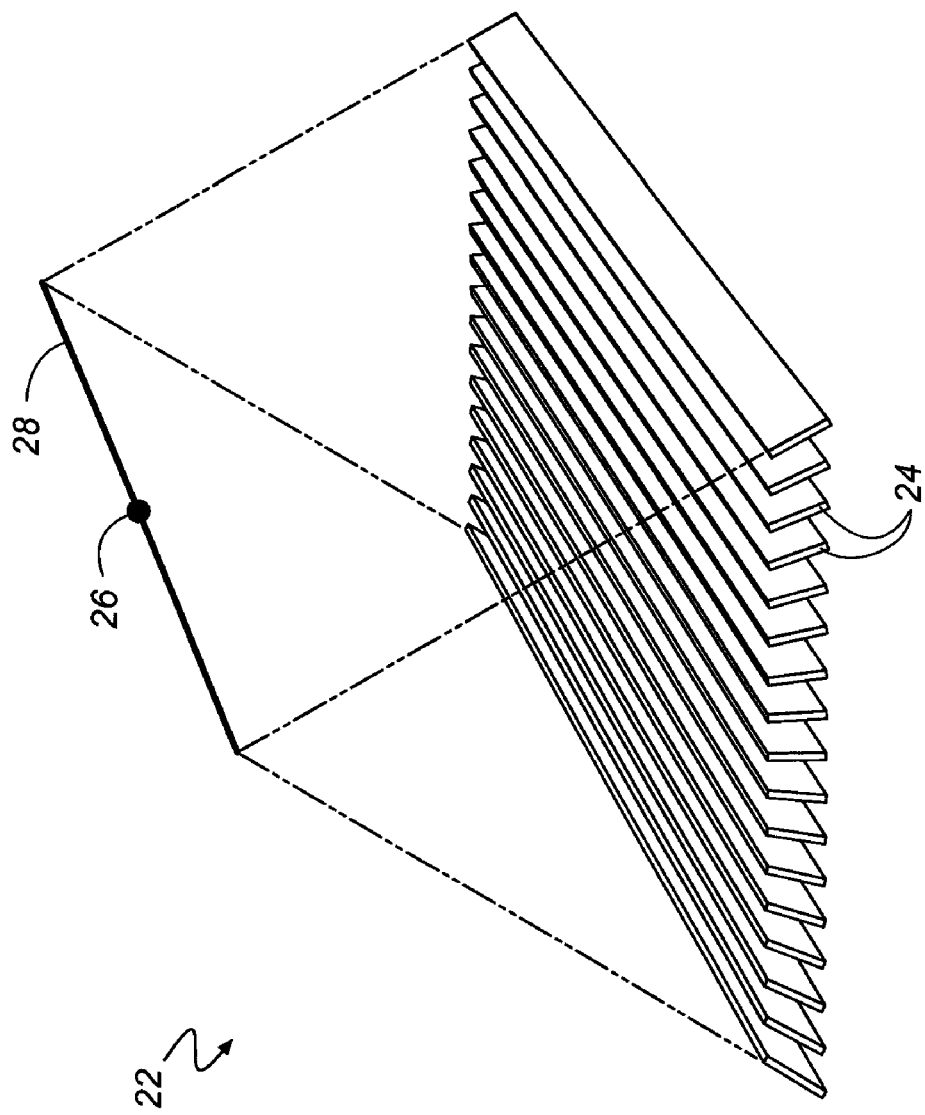
FIG. 2 is a perspective view showing an antiscatter grid conventionally provided to support x-ray imaging.

FIG. 2 shows an antiscatter grid 22 that is conventionally provided between cassette 20 and radiation source 14 to support x-ray imaging. Grid 22 presents another practical concern for alignment. The grid typically includes a series of lead strips 24 encased in an aluminum or carbon fiber material. The effectiveness of antiscatter grid 22, namely its ability to reduce the contribution of scattered radiation in an x-ray image, is dependent upon the relative position and orientation of both the grid and radiation head 12. Strips 24 are generally parallel along their lengths, but are angled toward a focal line 28. It is desirable to arrange a focal spot 26 for positioning radiation head 12 along focal line 28.

Figure 3:
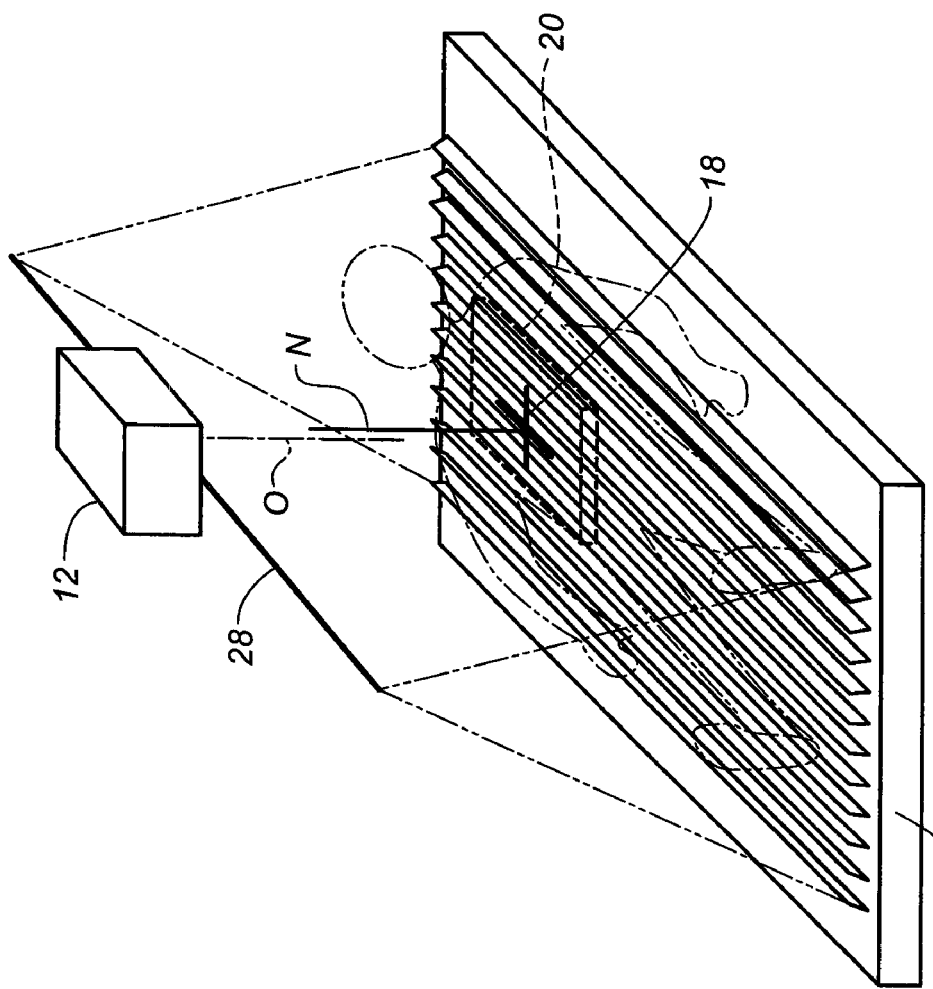
FIG. 3 is a perspective view showing alignment of a radiation head along the focal line of an imaging system, plus the positions of the patient and grid components relative to the central axis of the radiation source.
Figure 4B:
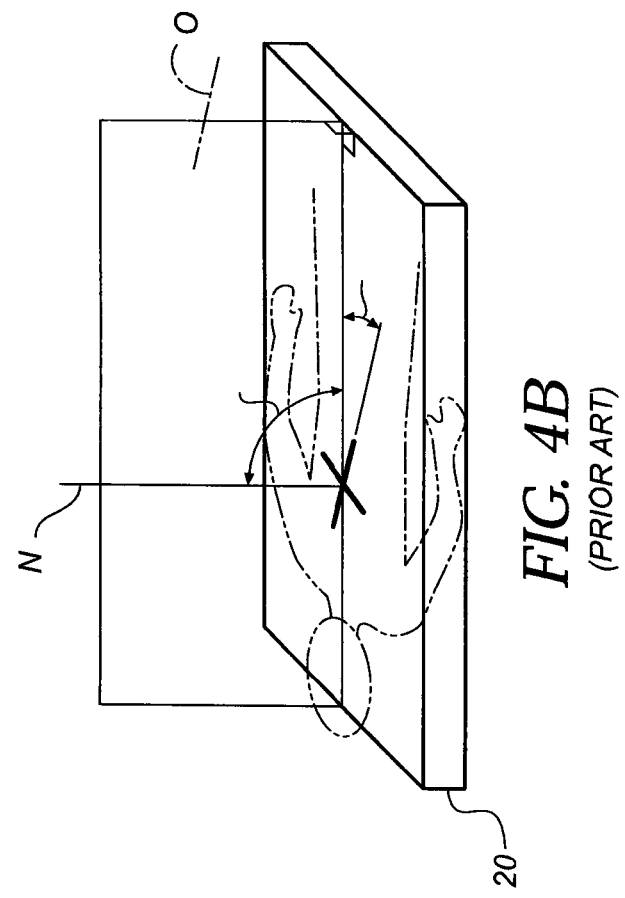
FIGS. 4A and 4B are perspective views showing, from two orthogonal perspectives, key angles of interest for achieving suitable imaging conditions.
Figure 4A:
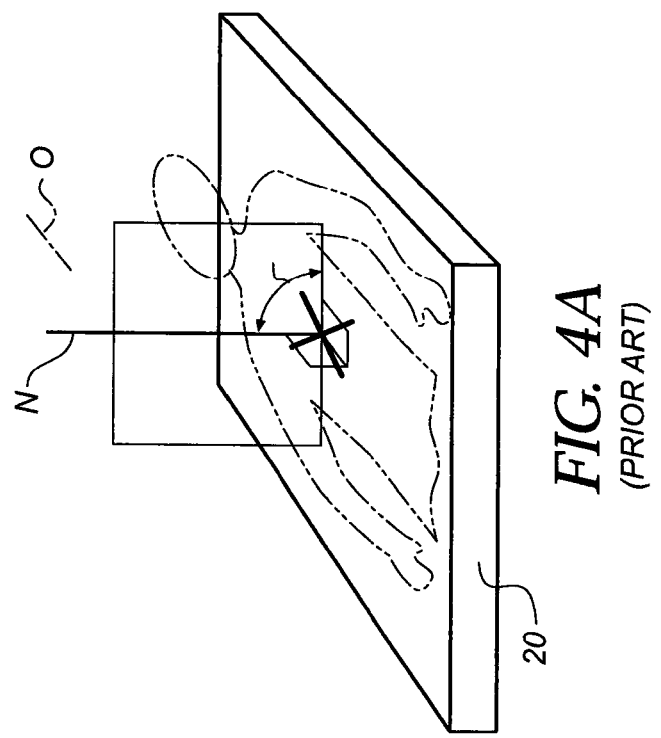

FIG. 3 shows one example of how radiation head 12 aligns along focal line 28 and indicates the relative positions of axis O and normal N. FIGS. 4A and 4B show, from two perspectives, key angles of interest for achieving suitable imaging conditions. The FIG. 4B view is in the same plane as the FIG. 4A view, but rotated 90 degrees. An angle α represents one angular component of the beam directed from the radiation source; an angle β represents another component of the beam. An angle γ represents rotation about normal N. Given these angles, it can be appreciated that more than mere tilt measurement will be needed to obtain proper alignment of cassette 20 and radiation head 12.

Figure 5:
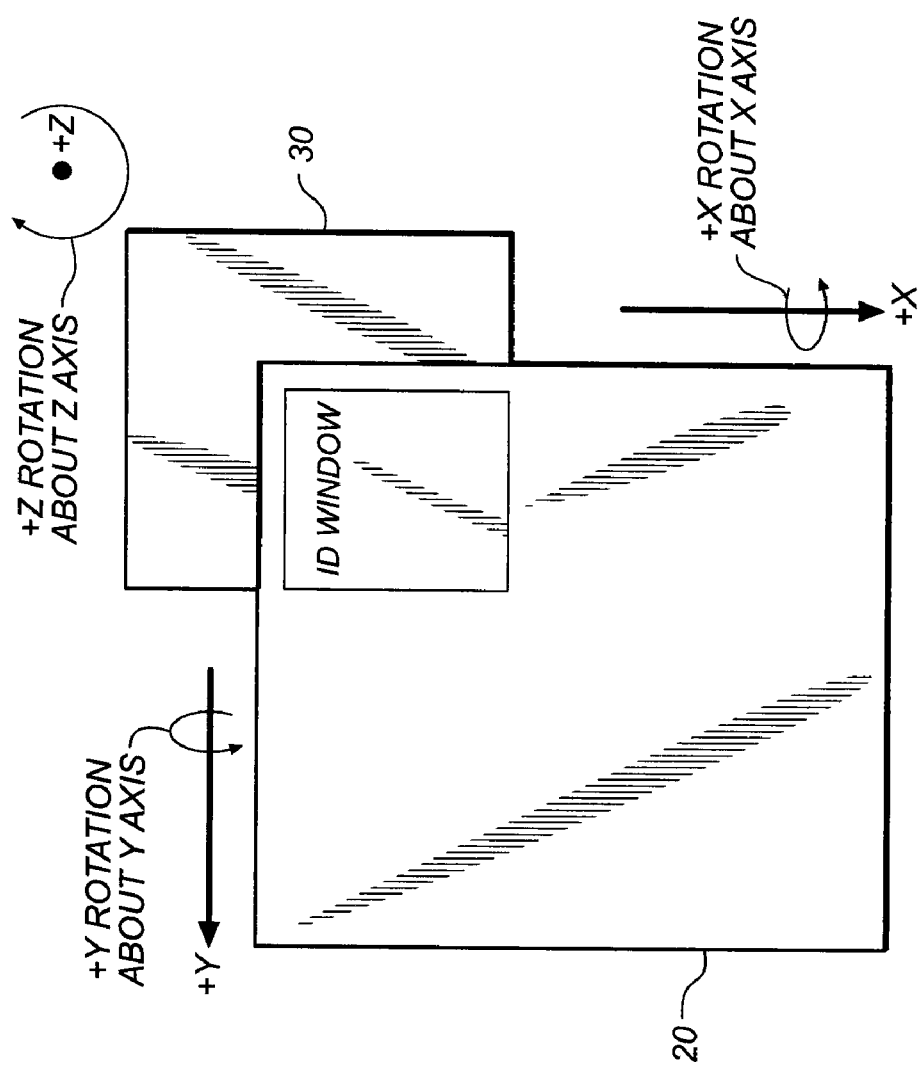
FIG. 5 is a plan view showing the sensor of the present invention attached to an x-ray cassette and the reference angles measured in one embodiment.

The present invention provides a solution to the positioning and angular orientation problem using three-axis measurement, preferably with inertial sensors. FIG. 5 shows a sensor apparatus 30 according to one embodiment, coupled to the corner of cassette 20. Sensor apparatus 30 preferably is of the inertial type that measures angular rate and acceleration for orthogonal x, y, and z axes, with the designations shown.

Components and functions of a suitable sensor apparatus are described later in this specification.

Angular rate sensors are widely used in airborne and vehicular apparatus for providing information on dynamic motion. To provide this type of information, angular rate sensors measure angular rates of rotation about particular axes and this data can be used to provide dynamic measurement of orientation angle. An angular rate sensor does not directly measure angle or orientation by itself, however, but measures rotational motion, that is, rotational speed. Integration of this motion over time then provides a measure of angle as a function of time. Unlike simple tilt sensors that merely report an angular difference with respect to gravity, angular rate sensors provide a complex amount of information that is continuously updated as the sensors are moved. This information can be used to obtain data on the angular difference with respect to directions other than the direction of gravity.

Figure 6A:
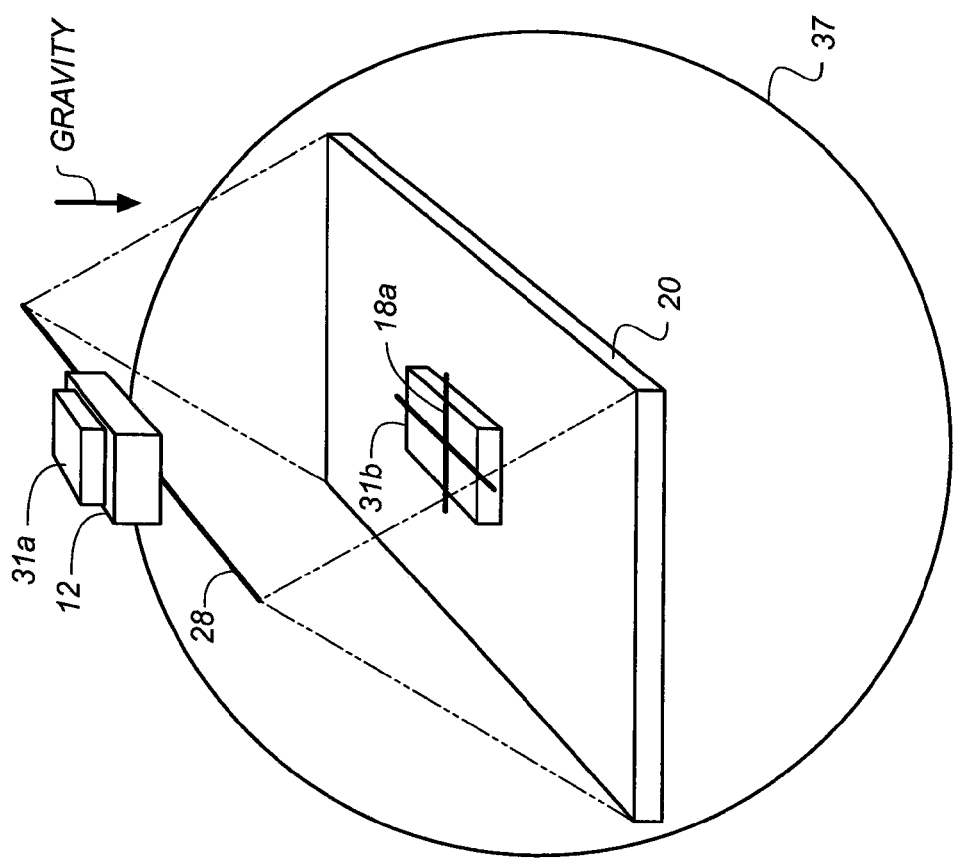
FIG. 6A shows a perspective view of the relationship between the x-ray head, a cassette in a level orientation, and the direction of gravity.
Figure 6B:
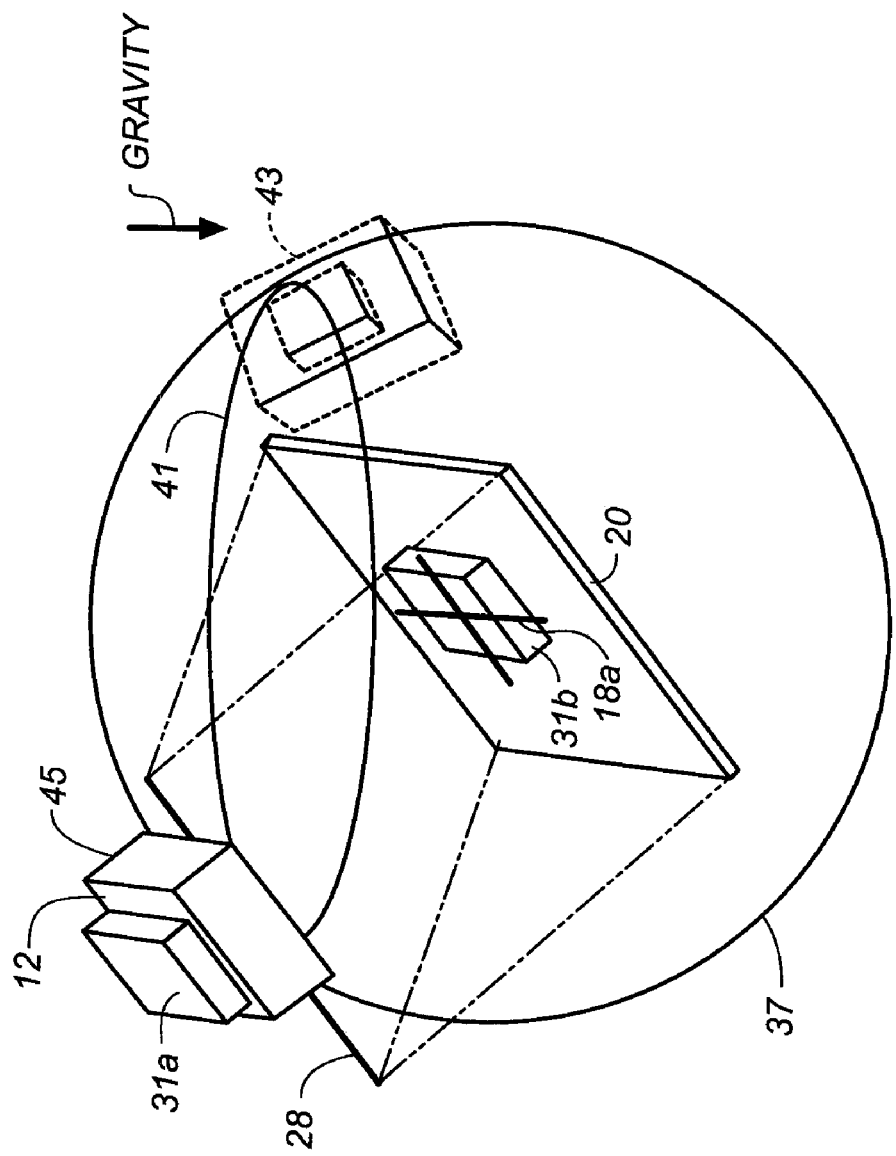
FIG. 6B shows a perspective view of the relationship between the x-ray head, a cassette in a non-level orientation, and the direction of gravity.

FIGS. 6A and 6B show graphically how the inertial measurement sensor apparatus of the present invention is advantaged over tilt sensors as described by Tanaka et al. and as used commercially in the Siemens Mobilett unit and other equipment. FIG. 6A shows the limited conditions under which a tilt sensor 31 can provide an acceptable solution. In the arrangement of FIG. 6A, cassette 20 is in a level orientation with respect to gravity. X-ray radiation head 12 projects a target light beam that is used to point radiation head 12 to the center of cassette 20. In terms of angular orientation, radiation head 12 is always oriented to provide its beam at a normal to the surface of cassette 20 and cassette 20 must be level. A conceptual orientation sphere 37 can be visualized as shown in FIG. 6A, centered at target 18a on cassette 20 and having its radius as the distance between radiation head 12 and the center of target 18a. Relative to conceptual orientation sphere 37, radiation head 12 can be in a single position only, as shown, so that the radiation beam is correctly pointed. Tilt sensor 31a can be mounted to x-ray radiation head 20 to indicate that x-ray radiation head 12 is oriented correctly, along focal grid line 28. Tilt sensor 31a indicates that x-ray radiation head 12 is in a level orientation. The distance from x-ray head 12 to the cassette 20 is adjusted to the focus distance of the grid. Thus, for the arrangement shown and described with reference to FIG. 6A, tilt sensors 31a at radiation head 12 and 31b at cassette 20 would be sufficient for providing the correct orientation for imaging.

FIG. 6B illustrates what happens if the tilt sensor solution that works for the limited conditions shown in FIG. 6A is applied in a more general case. In the arrangement of FIG. 6B, the same imaging components as those shown in FIG. 6A are used, but are oriented at a non-level angle relative to the direction of gravity. Here the tilt of cassette 20 is again measured with tilt sensor 31b. With this angle, relative to gravity, radiation head 12 may be in any position along a circle of uncertainty 41 shown on sphere 37 while its tilt sensor 31a reads the same tilt value as given in the initial reading of the tilt of cassette 20. For example, tilt sensor 31a would report tilt at a position 43, shown dotted in FIG. 6B, as the same as tilt at a position 45. This shows that tilt sensors 31a and 31b are incapable of providing information needed for achieving proper angular orientation of both x-ray radiation head 12 and cassette 20, except for the singular case when cassette 20 is level, as was described with reference to FIG. 6A. It can be observed that FIG. 6A also has a circle of uncertainty; however, this is positioned at the top of sphere 37 and is effectively small enough to be considered as a point. Orientation sensing using an inertial sensor apparatus 30 as in FIG 5, however, can provide sufficient information for achieving proper orientation of radiation head 12 and cassette 20 for the general conditions shown in FIG. 6B.

Figure 7A:
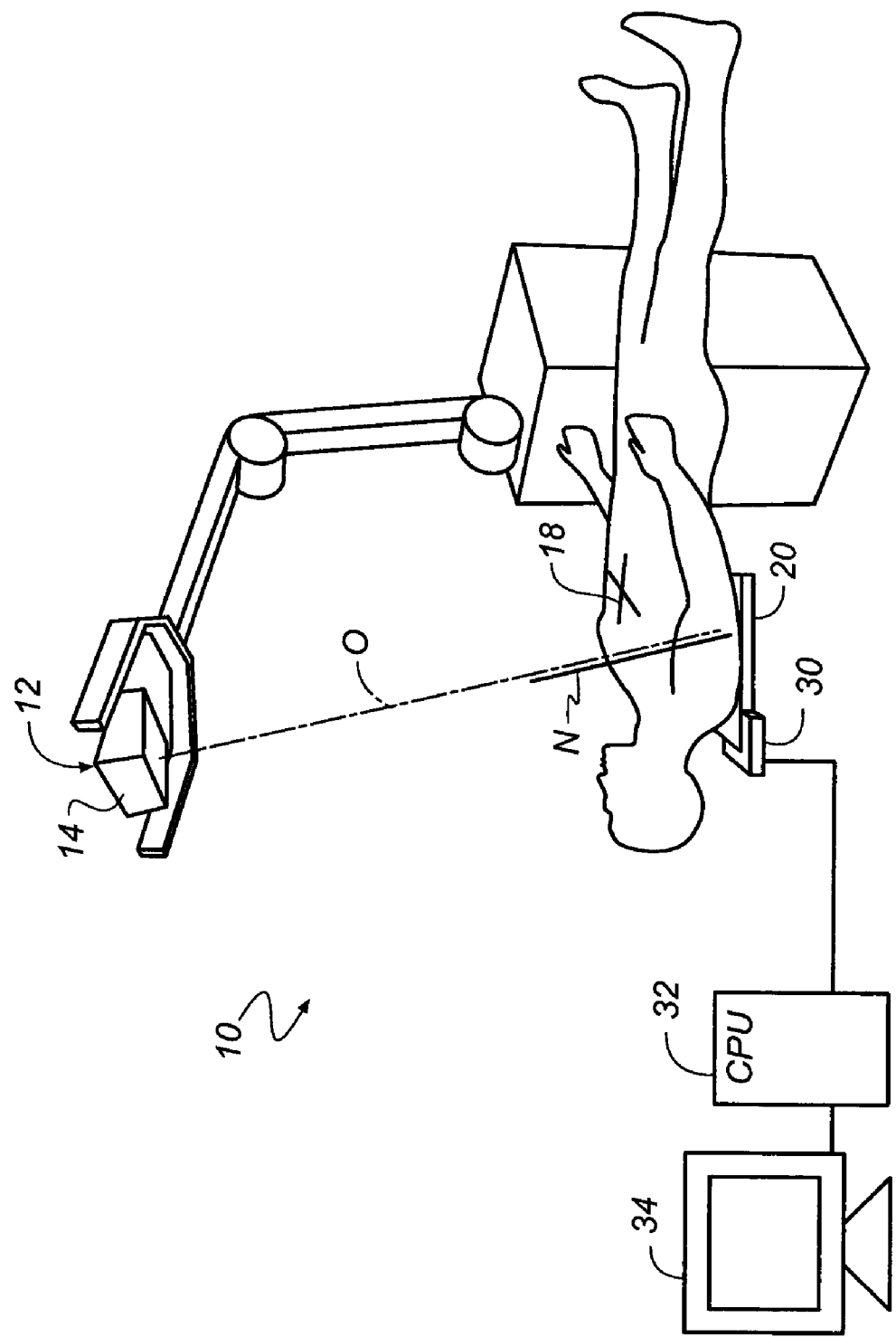
FIG. 7A is a perspective view of an imaging system of the present invention in one embodiment, with a measurement sensor disposed on the cassette.
Figure 7B:
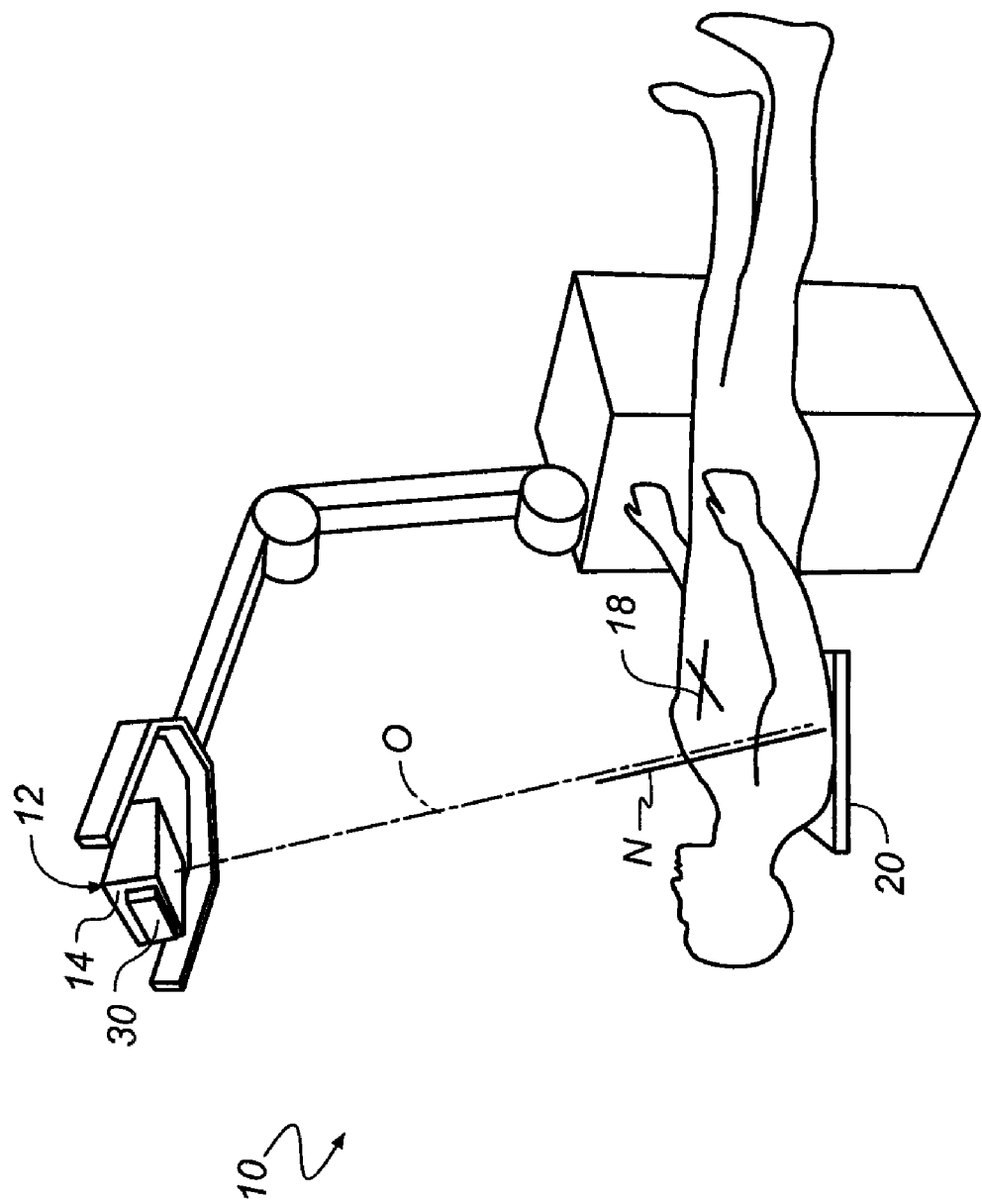
FIG. 7B is a perspective view of an imaging system of the present invention in another embodiment, with a measurement sensor disposed on the radiation head.

FIGS. 7A and 7B show how sensor apparatus 30 is used, according to one embodiment. Initially, in FIG. 7A, sensor apparatus 30 is adapted to be coupled to cassette 20 for obtaining a reference frame angular orientation measurement. Once this reference angular orientation measurement is obtained, sensor 30 can be de-coupled from cassette 20 and is adapted to be sequentially coupled to radiation head 12, as is shown in FIG. 7B. Sensor apparatus 30 now reports to the technician, as described later in this specification, providing its differential angular orientation information relative to the reference angular orientation measurement that was initially made when it was coupled to cassette 20 (FIG. 7A). See the subsequent description regarding FIGS. 13 to 17. This differential angular orientation information can then be used by the technician for adjusting the angular orientation of radiation head 12 to achieve the proper differential angle for the reference position of cassette 20 while target 18 is simultaneously pointed toward a suitable position. An optional computer workstation 32 and display 34 may be in communication with sensor apparatus 30 for tracking, computation, and reporting information to the technician, as is described subsequently. Optionally, control logic can be self-contained within the sensor apparatus 30.

Figure 8:
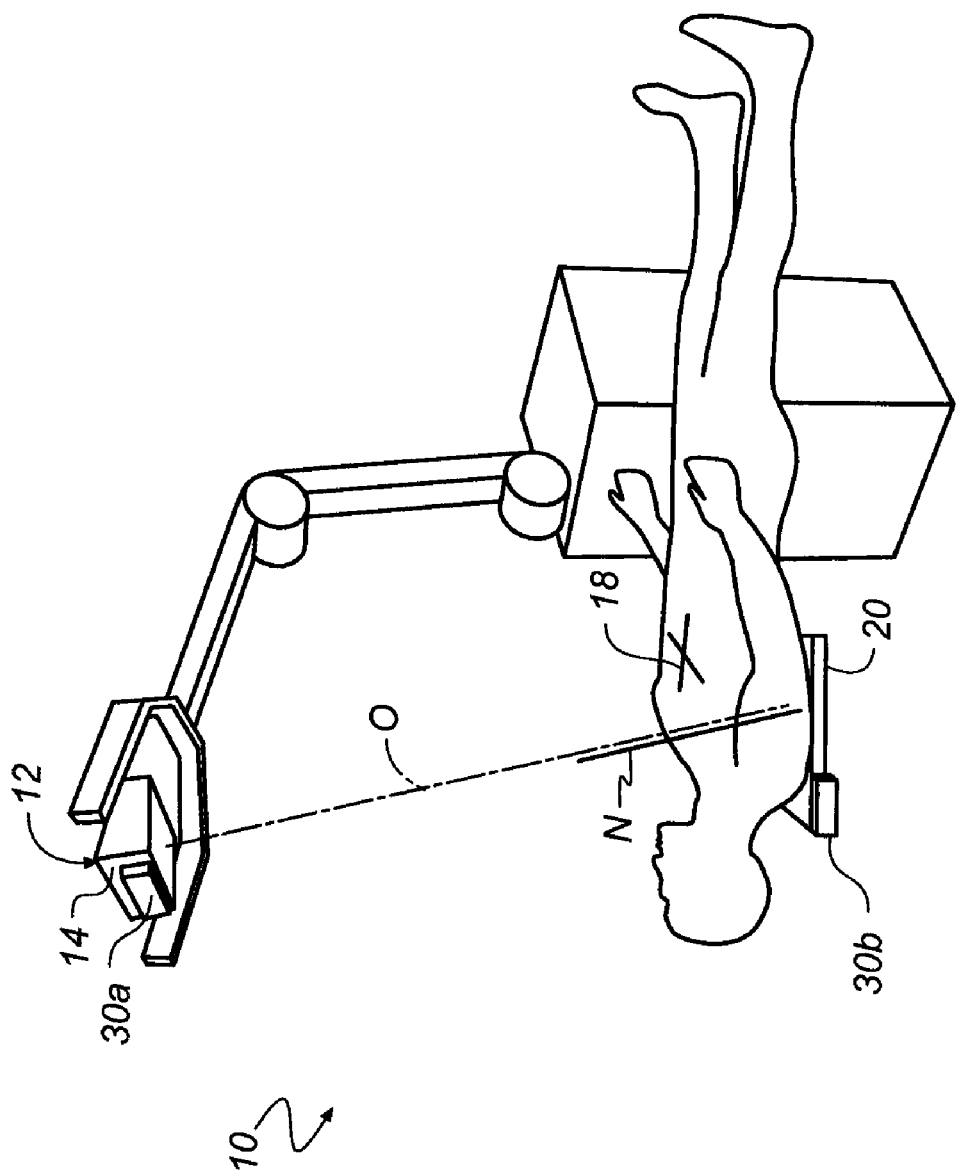
FIG. 8 is a perspective view of an imaging system of the present invention in an alternate dual-sensor embodiment, with one sensor disposed on the cassette and the other sensor, on the radiation head.

FIG. 8 shows how sensor apparatuses 30a and 30b are used in an alternate embodiment. Here, an initial calibration is performed in order to align sensor apparatuses 30a and 30b so that both share the same reference setting. See the subsequent description regarding FIG. 17. Then, sensor apparatuses 30a and 30b can communicate to control logic what adjustments need to be made in order to achieve differential angular alignment. As in the FIG. 7A/7B embodiment, an external computer workstation 32 and display 34 may be used for this dual sensor 30a/30b embodiment.

Mounting Arrangements

Figure 10:
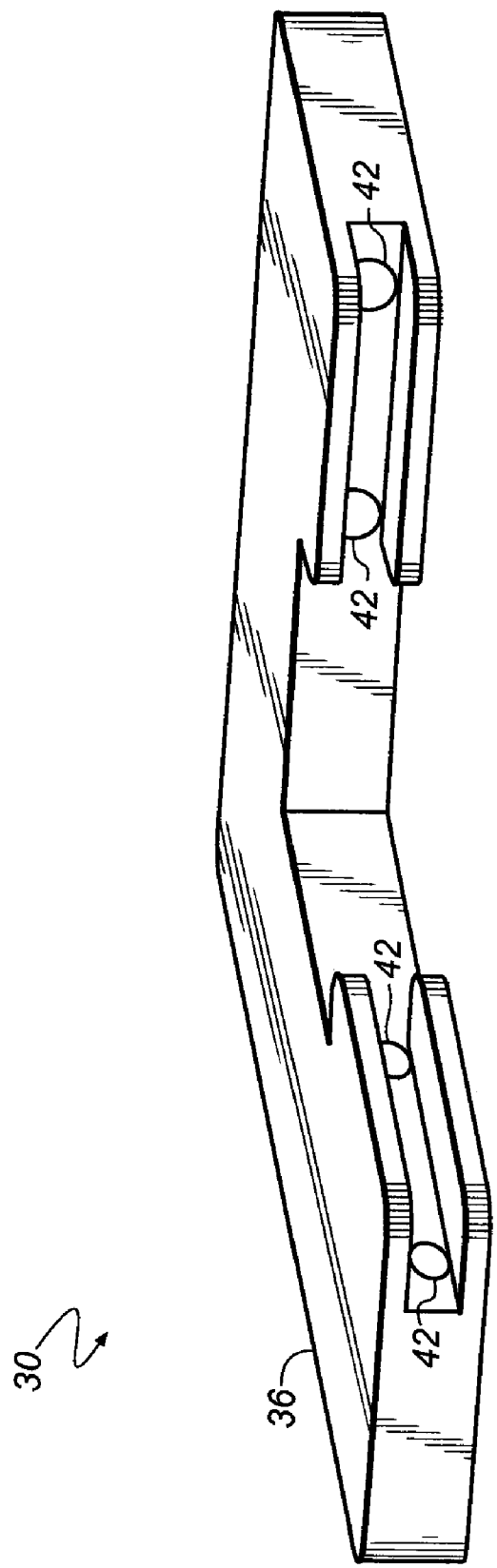
FIG. 10 is a perspective view of another embodiment of the housing of the sensor, in which magnets are used for coupling the sensor to components of the radiation imaging system.

For either the single- or dual-sensor embodiments, sensor apparatus 30 can be coupled to cassette 20, and thus to the photostimulable medium that records the image, in a number of ways. In addition, there are a number of options for coupling sensor apparatus 30 to radiation head 12. FIGS. 9A and 9B show perspective and end views for one embodiment, in which sensor apparatus 30 has a housing that is featured to fit onto a corner of cassette 20. Opposing pairs of tabs 38 extend from housing 36 and provide the mechanism for maintaining a snug pressure fit against cassette 20, whereby the technician can readily manually attach or remove sensor apparatus 30. A pressure fit may be acceptable for registering sensor apparatus 30 to cassette 20; however, other embodiments can also be used. FIG. 10 shows housing 36 having a fitting arrangement using magnets 42 that would be attracted to metal structures in cassette 20.

Figure 11:
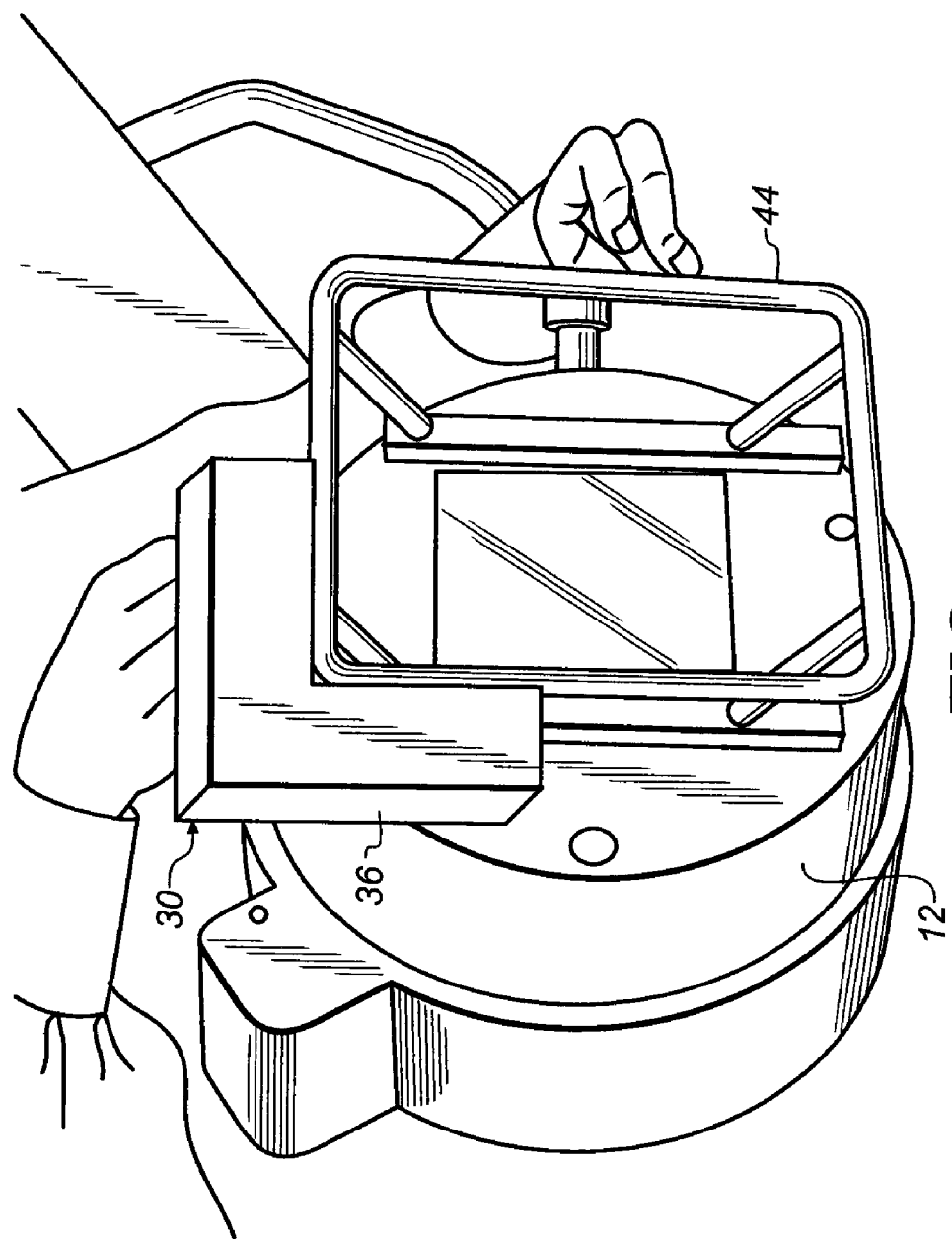
FIG. 11 is a perspective view of a radiation head that has the sensor of the present invention mounted thereon, in one embodiment.
Figure 12:
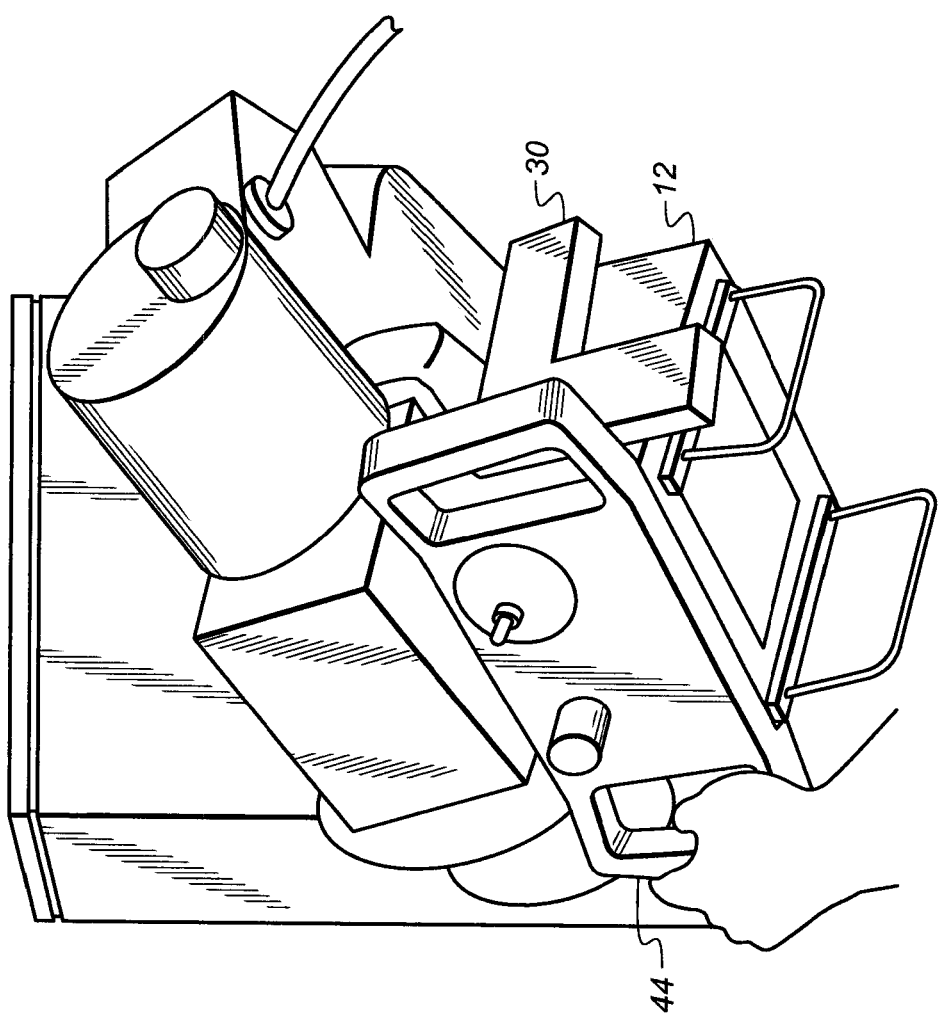
FIG. 12 is a perspective view of a radiation head that has the sensor of the present invention mounted thereon, in an alternate embodiment.

As was described with reference to the embodiments of FIGS. 7B and 8, it is also necessary that sensor apparatus 30 be mounted to radiation head 12 during adjustment of head angle. The same fitting or some alternative fitting may be used for this purpose. Referring to the perspective view of FIG. 11, there is shown an embodiment with sensor apparatus 30 coupled to a handle 44 of radiation head 12. This may use the pressure fit of FIGS. 9A and 9B or may use the magnetic approach shown in FIG. 10, for example. Other types of fitting could be used, including, for example, pin-and-socket fitting, conventional thumbscrew or latched fasteners, and the like. It would be a significant advantage for sensor apparatus 30 to mount against either or both cassette 20 and radiation head 12 without requiring the use of tools. Because the apparatus of the present invention is intended to be a suitable retrofit for existing systems, it is important that sensor apparatus 30 be coupled to either cassette 20 or radiation head 12 without requiring redesign of these components. Flexible hook-and-loop or hook-and-pile connectors, such as VELCRO fasteners from Velcro Industries B. V., Amsterdam, NL, or some other type of separable flexible fastening device could alternately be used for coupling sensor apparatus 30 to either cassette 20 or to radiation head 12 or both. The perspective view of FIG. 12 shows another embodiment, with sensor apparatus 30 attached to the side of radiation head 12. In this case, computation must take into account the different orientations of sensor apparatus 30 with respect to cassette 20 and radiation head 12.

In order to allow periodic recalibration of sensor apparatus 30 components, it is desirable that the coupling method that is used allow for easy attachment and removal of sensor apparatus 30 from its mounted position. This is particularly true for the embodiment shown in FIGS. 7A and 7B, where a single sensor apparatus 30 is shared between both cassette 20 and radiation head 12. By the nature of the types of inertial sensing components used, there is a time limitation imposed before sensor apparatus 30 may lose accuracy due to drift and noise.

It can also be appreciated that coupling housing 36 to an individual make and model of radiation head 12 may require an additional bracket or other hardware. Each model of radiation head 12 can have a unique design, requiring a unique solution for making this attachment.

At cassette 20, it is generally preferred to mount sensor apparatus 30 against a corner of the housing of the cassette, as shown in FIGS. 5 and 9A, for example. Or, it may be desirable to mount sensor apparatus 30 along an edge. However, other arrangements are possible, including arrangements wherein sensor apparatus 30 is not removable, but is built in to cassette 20 in some way.

Components of Sensor Apparatus 30

Figure 13:
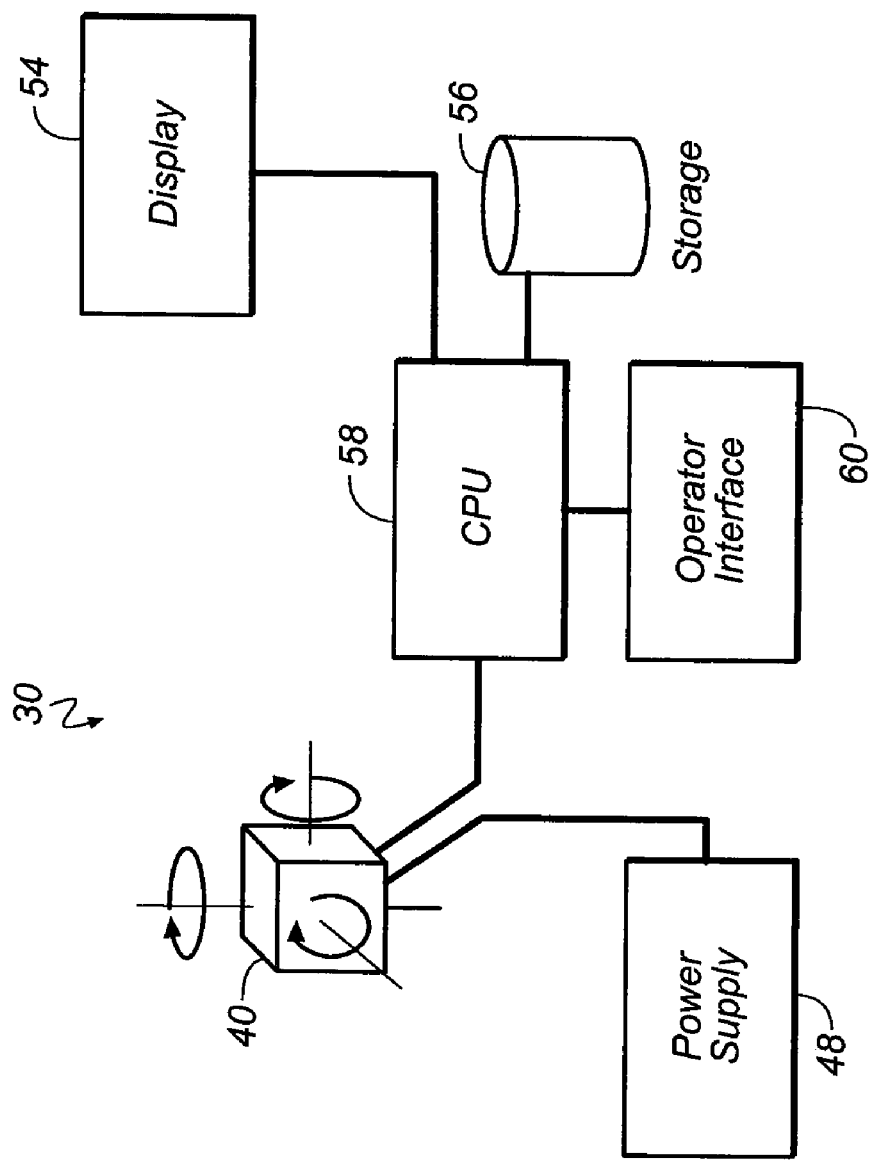
FIG. 13 is a block diagram showing key components of the sensor apparatus of the present invention.

Referring to FIG. 13, there is shown a block diagram of the basic components of one embodiment of a sensor apparatus 30. At the core of sensor apparatus 30 is a sensor module 40 that provides inertial sensing for angular rate and acceleration with respect to three orthogonal axes, conventionally x, y, and z as was shown in FIG. 5. There are a number of types of devices that could be used for sensor module 40, including Micro-ElectroMechanical Systems (MEMS) devices. One of these devices, for example, is the FalconGX 6DOF Sensor Module, a product of O-Navi LLC, Micro Avionics Group, San Diego, Calif. This device exhibits the behavior described earlier with respect to FIG. 5, reporting angular rate and acceleration along mutually orthogonal x, y, and z axes, with increased output corresponding to movement in the directions indicated by arrowheads in FIG. 5. Sensor module 40 may also detect other conditions, such as proper operating temperature (indicating warmup is completed and equipment accuracy can be assumed).

Because it detects angular rotation rate and acceleration, rather than merely tilt, sensor module 40 runs continuously, receiving power from a power supply 48, typically some type of battery or other storage cell. Alternately, AC power could be provided externally and converted to the needed DC levels; however, portable power has significant advantages for handling and ease of use. A control logic processor 58 is in communication with sensor module 40 for obtaining the angular rate and acceleration data at regular sampling intervals. With the FalconGX module, for example, sampling can be performed at 50 times per second. Control logic processor 58 may be an on-board microprocessor or other dedicated control logic device. Alternately, such as when a high degree of computation is required, a communication link may be provided to an external processor, such as a computer workstation or other device. Storage 56 can be provided for maintaining a memory storage buffer of some portion of the sampled data from sensor module 40. A display 54 of some type is provided as an indicator responsive to orientation data from sensor module 40 and providing some visible and/or audible indication of relative angular orientation, as an aid to help the technician to ascertain in which direction adjustment is needed. A technician interface 60 is provided and may include a control console for command entry, plus such devices as reset or zeroing switches used for calibration, for example.

It can be appreciated that the basic model presented in FIG. 13 allows for any number of alternate arrangements. Sensor apparatus 30 in FIG. 13 provides a complete system, but one or more components may be located remotely, rather than integrated on the same circuit board, for example, used for sensor module 40. Other components may be optional or allow a wide scope for embodiment. For example, control logic processor 58 can use an external device or system, or the function of control logic processor 58 can be distributed among one or more separate processors. Similarly, storage 56 can be located on a single device or may be stored on a host workstation or other device that provides processing computation for sensor 30. Display 54 can be mounted directly onto housing 36 or may be a conventional Cathode-Ray Tube (CRT) display, such as one connected as part of a conventional computer workstation. Or, display 54 can be simply a numeric display device, using patterned Light-Emitting Diodes (LEDs) or other devices to display values for any or all of the motion sensed by sensor module 40.

In the dual-sensor embodiment shown in FIG. 8, both sensor apparatuses 30 could have the same design, with appropriate programming that designates one sensor apparatus 30b as the benchmark (mounted on cassette 20 in most cases) and the other sensor apparatus 30a as variable. Thus, for example, display 54 on the benchmark unit may be zeroed or blank; on the other sensor 30 that attaches to radiation head 12, display 54 would be active.

The function of display 54 could be enhanced or replaced by an audible tone or signal of some kind. For example, a variable audio tone or clicking may be used to indicate to the technician that adjustment is needed in one or more directions or that suitable adjustment has been achieved.

Figure 14:
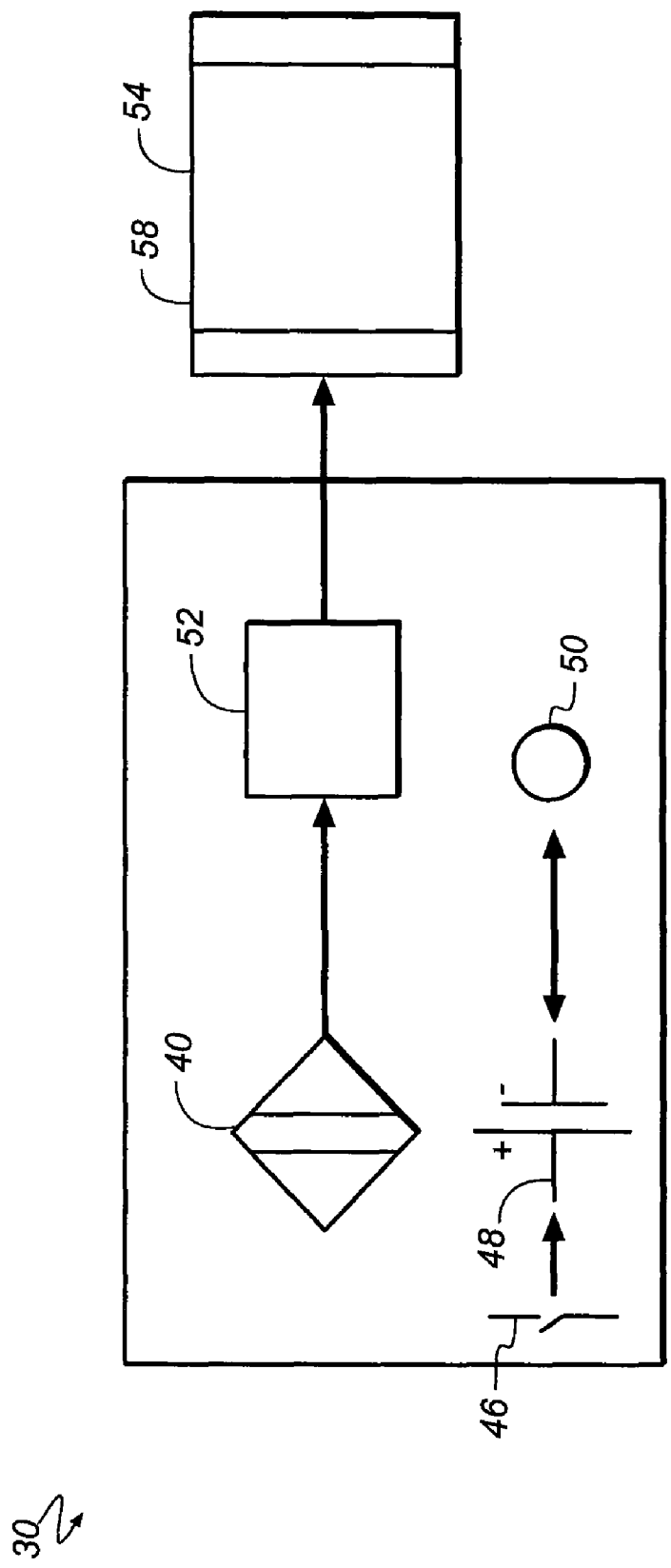
FIG. 14 is a block diagram showing key components of the sensor apparatus of the present invention in an embodiment that utilizes a remotely located display component.

The schematic block diagram of FIG. 14 shows one embodiment following the basic model given in FIG. 13. Here power supply 48 is a battery. A power switch 46 is provided, as is a power indicator 50. A communications circuit 52, such as a wireless RF transceiver or, alternately, a wired communications module, enables transmission of measurement data from sensor module 40 to an external device. In the embodiment of FIG. 14, this data goes to external control logic processor 58 and its corresponding display 54.

The embodiment shown in FIG. 14 could be useful, for example, where signals from sensor apparatus 30 would be communicated to a device or devices for making automated orientation adjustments. Thus, for example, sensor apparatus 30 could be in communication with a series of motors and motion control devices, such as for the sensor apparatus 30a component coupled to radiation head 12 in the embodiment of FIG. 8.

Figure 15:
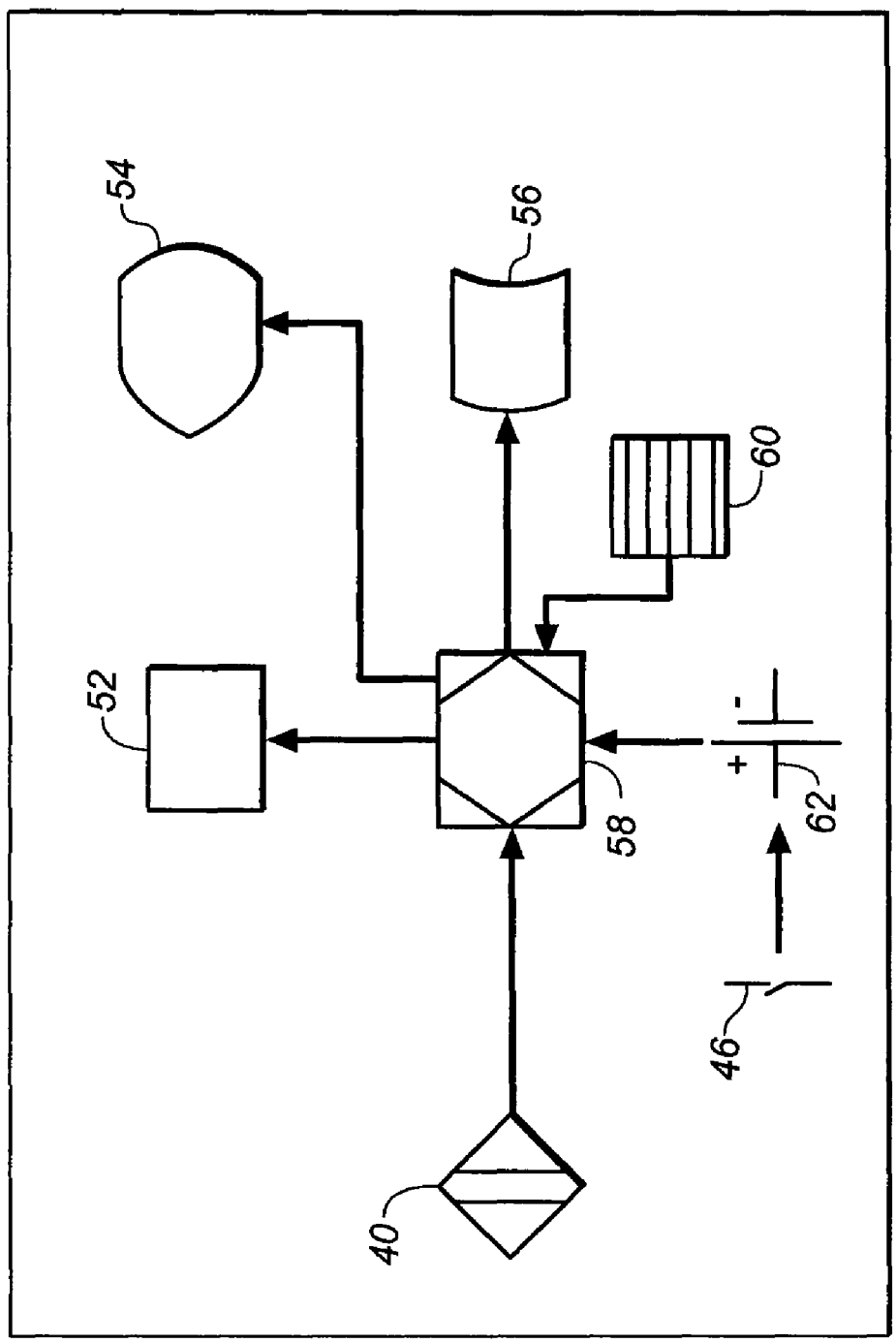
FIG. 15 is a block diagram showing key components of the sensor apparatus of the present invention according to another embodiment.

The schematic block diagram of FIG. 15 shows another embodiment of sensor apparatus 30, again following the basic model given in FIG. 13. In this embodiment, sensor module 40 connects to a local control logic processor 58, but can also communicate through communications circuit 52 to some other computer or similar control logic device as well. Technician interface 60 includes a touchpad for entering desired values or for zeroing sensor apparatus 30 at the beginning of a positioning cycle. Display 54 is provided directly on sensor apparatus 30 in this embodiment.

Control logic processor 58 functions typically include transmitting control signals to sensor module 40 and obtaining the regularly updated data from this component. Other functions such as reset and calibration can also be performed through commands from control logic processor 58, thus enabling remote reset, for example. Algorithms for computing angle based on the sensor data may be stored and executed on control logic processor 58 on sensor apparatus 30 itself. However, it can be more advantageous to transmit this data to an external computer workstation or other processor for efficient processing and display.

The embodiments shown in FIGS. 14 and 15 can be used to provide movement information to, or to obtain commands from, a number of different types of external devices, both wireless and wired. For example, communications circuit 52 can be used to display or provide motion information to a hand-held computer or personal communications device, such as a cell phone, Personal Digital Assistant (PDA), and the like. In this way, orientation information and commands can be viewed and entered on a remote device that is easily accessible to the technician.

Operating Options

For the basic single- and dual-sensor embodiments shown in FIGS. 7A/7B and 8 respectively, it is useful to consider the sequence of operations performed by the technician in order to set up the position of the radiation image detection device (cassette 20) and radiation head 12. Turning now to the flow chart of FIG. 16, the basic steps for system operation with the single sensor embodiment are shown.

In a sensor setup step 100, the technician first mounts sensor apparatus 30 on the side of cassette 20 and positions cassette 20 in the desired position for the image that is needed. The technician then uses the aiming light beam on the unit to project target 18 (FIG. 1) on the patient, to ensure that the cassette and radiation head are properly positioned relative to each other for image capture. A reset step 110 then follows, in which the technician zeroes sensor apparatus 30 by pressing a switch or making some other suitable command entry. This sets the stable angular orientation of sensor apparatus 30 as the benchmark orientation. Motion from this point can be calculated by processor 58 to determine how much sensor apparatus 30 is shifted angularly away from this original orientation at a later point in time.

In a sensor repositioning step 120, the technician removes sensor apparatus 30 from its position and orientation on or alongside cassette 20 and second attaches it to the appropriate structures on radiation head 12. Next, a feedback review step 130 is executed, during which the technician reviews the feedback generated by sensor apparatus 30 in its position against radiation head 12. The outputs of sensor apparatus 30 will be indicative of its change in orientation from its benchmark orientation at cassette 20. From those outputs, the technician determines how to align radiation head 12 properly to cassette 20. Where an oblique angle of incidence is desired, as in the case shown in FIGS. 4A and 4B for example, the technician carefully aligns the angle of radiation head 12 and aims target 18 appropriately.

In a decision step 140, the technician determines whether or not the adjustment is suitable and imaging can proceed. Where additional adjustment is necessary, the technician carries out a head repositioning step 150 for making the minor adjustment. Where no additional adjustment is necessary, an image capture step 160 follows, during which the technician completes preparation and obtains the x-ray image.

Similar steps are followed for the dual-sensor embodiment. As shown in the logic flow diagram of FIG. 17, a base calibration step 200 is executed first. In this step, sensor apparatuses 30a and 30b are aligned to each other. This is most readily accomplished by simply holding sensor apparatuses 30a and 30 together in about the same position, then entering a base calibration command for each sensor apparatus 30a, 30b. This sets a benchmark condition, so that movement of either sensor apparatus 30a, 30b is relative to this initial position (aligned orientation), allowing computation of the angular orientation difference between sensor apparatuses 30a and 30b. A patient side setup step 210 is next executed. During this procedure, the technician mounts sensor apparatus 30b on the side of cassette 20 and positions cassette 20 in the desired position for the image that is needed.

An initial head position step 220 is then carried out. During this step, the technician makes initial adjustments to the orientation of radiation head 12, according to information provided from sensor apparatuses 30a and 30b. This may involve rotation about more than one axis as the technician observes displayed values on display 54 (FIGS. 13-15) to ascertain the proper direction and amount of movement needed.

Following procedures of initial head position step 220, the technician performs a decision step 230. Here, the technician determines whether or not the adjustment is suitable and imaging can proceed. Where additional adjustment is necessary, the technician carries out a readjustment step 240 and makes the desired minor adjustments. Where no additional adjustment is necessary, an image capture step 250 follows, during which the technician completes preparation and obtains the x-ray image.

Figure 16:
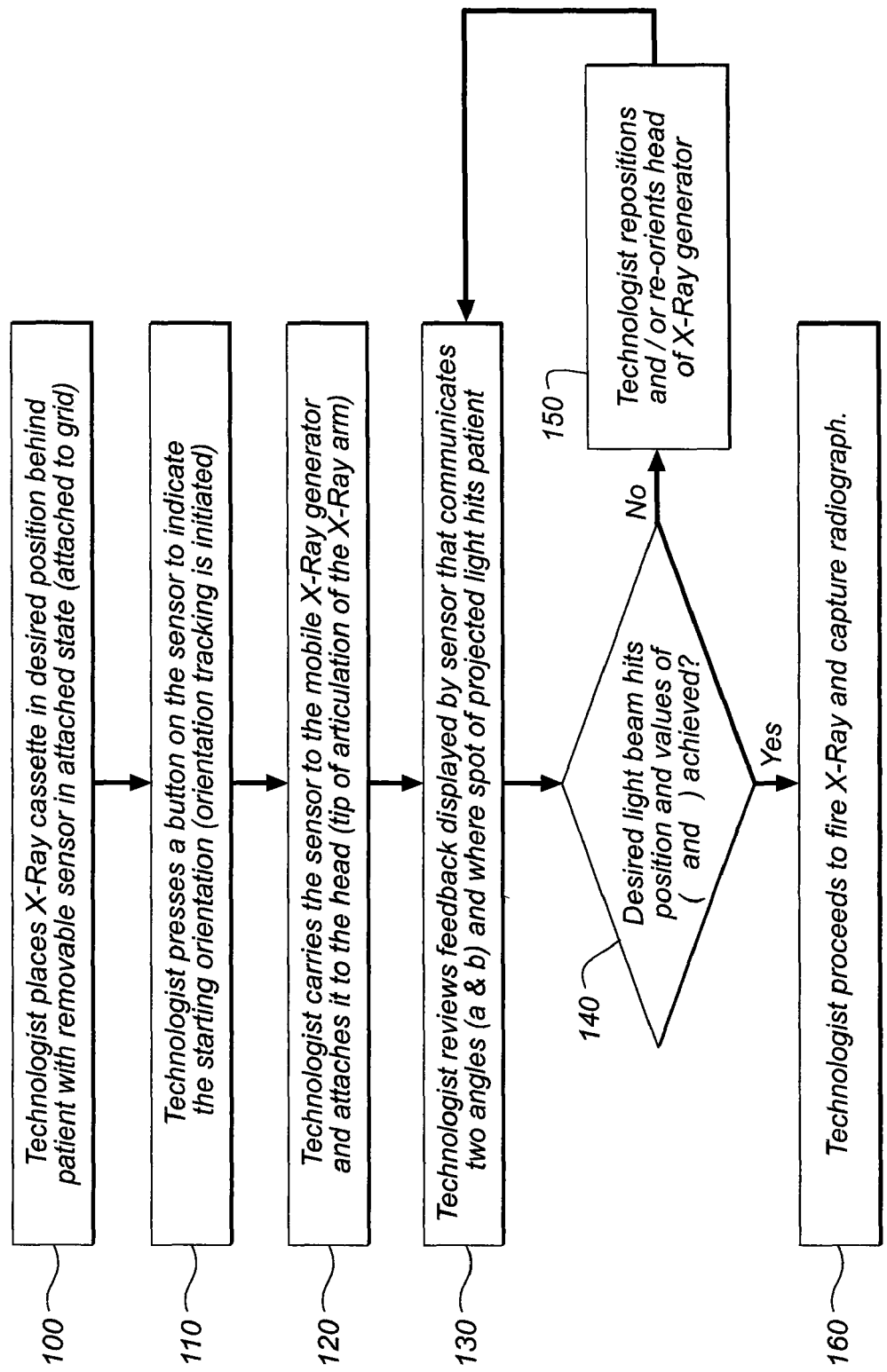
FIG. 16 is a logic flow diagram showing technician procedures for use of the sensor apparatus of the present invention in an embodiment where a single sensor is provided.
Figure 17:
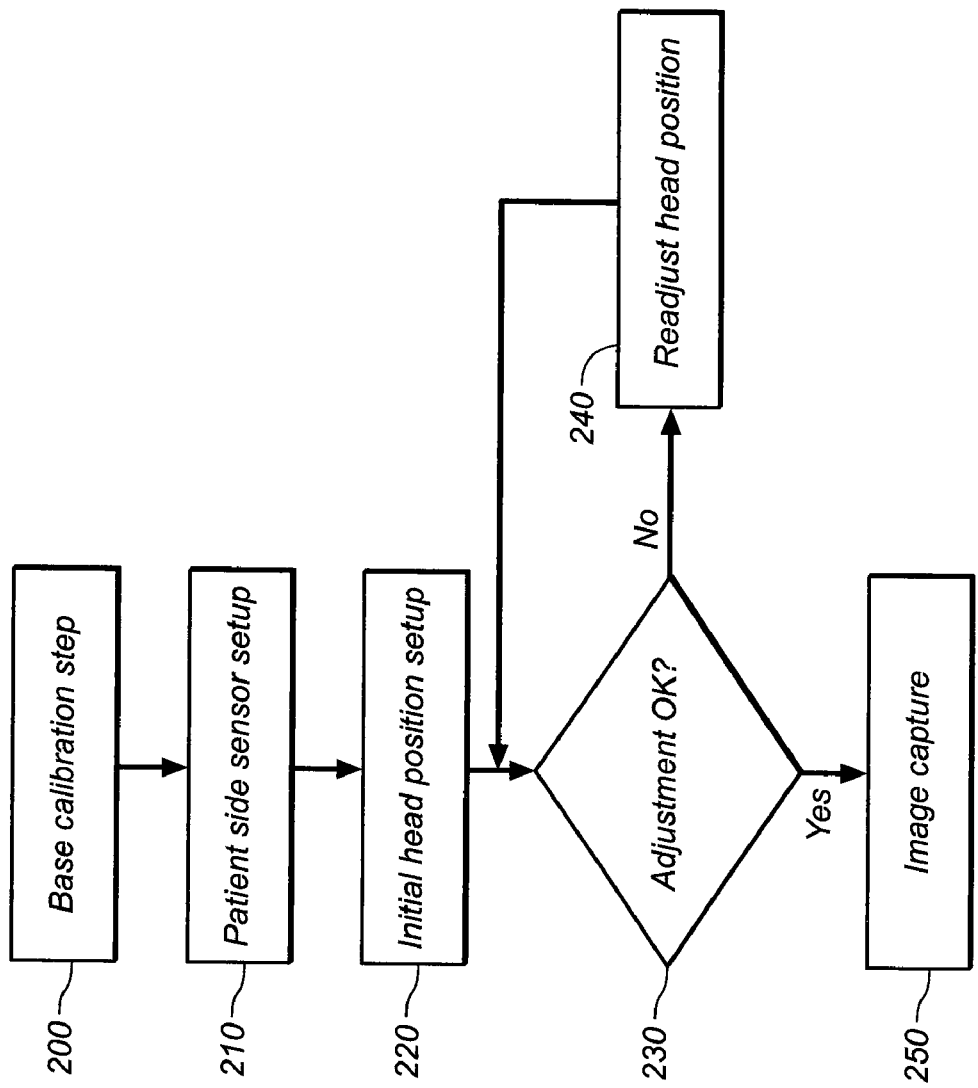
FIG. 17 is a logic flow diagram showing technician procedures for use of the sensor apparatus of the present invention in an embodiment where two sensors are provided.

It can be appreciated that the technician steps shown in FIGS. 16 and 17 are exemplary, provided to illustrate typical operation, and should not be considered as limiting; a number of other possible operation sequences could be executed. Also, it is instructive to note that there is a time factor involved, since accumulated error and noise can cause drift and lead to positional errors, as was noted earlier. It must be observed that there is always some element of noise and some element of error that can have a compounding effect, degrading calculation results over time. Thus, timeout would be one error condition not noted in FIG. 16 or 17, but capable of overriding technician procedures and requiring recalibration (that is, re-zeroing) of the device. Self-checks performed by sensor apparatus 30 include temperature measurement, to ascertain that the device has achieved a preferred operating temperature range. Sensor module 40 components are also sensitive to abrupt motion, such as if sensor apparatus 30 or cassette 20 were dropped or bumped during movement by the technician. An error condition of this type would prevent operation until recalibration (re-zeroing) is performed by the technician.

Display Options

Figure 18:
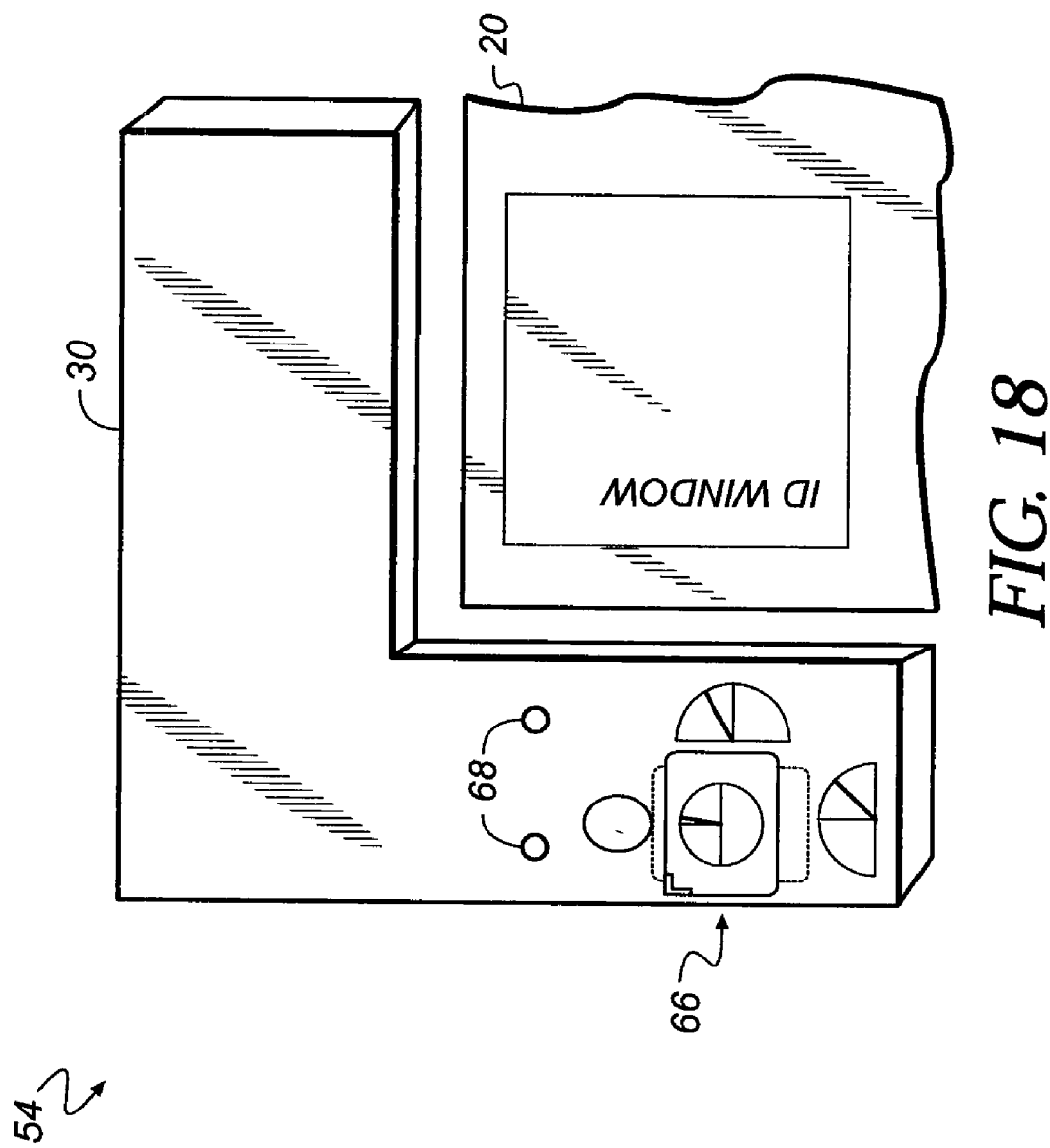
FIG. 18 is a view of the sensor of the present invention in an embodiment having the display integrated as part of the sensor body.

As indicated earlier, there are a number of options for providing the function of display 54 as described with reference to FIGS. 13-15. In one embodiment, shown in FIG. 18, sensor 30 has an on-board bank of indicators of various types that assist the technician in use of the device. Orientation displays 66, described subsequently in more detail, give a graphic indication of orientation data obtained with respect to each axis. Operational indicators 68 illuminate to indicate status of the power source or may indicate an error condition requiring recalibration. Embodiments with display 54 functions incorporated on sensor 30 itself would be particularly advantageous for either the single sensor arrangement of FIGS. 7A and 7B or the dual-sensor arrangement described earlier with reference to FIG. 8. With display 54 integrated as part of sensor 30, the technician can make adjustments of radiation head 12 orientation while viewing display 54 directly. In FIG. 8, for example, sensor 30a could have the built-in display 54 embodiment of FIG. 18.

Figure 19:
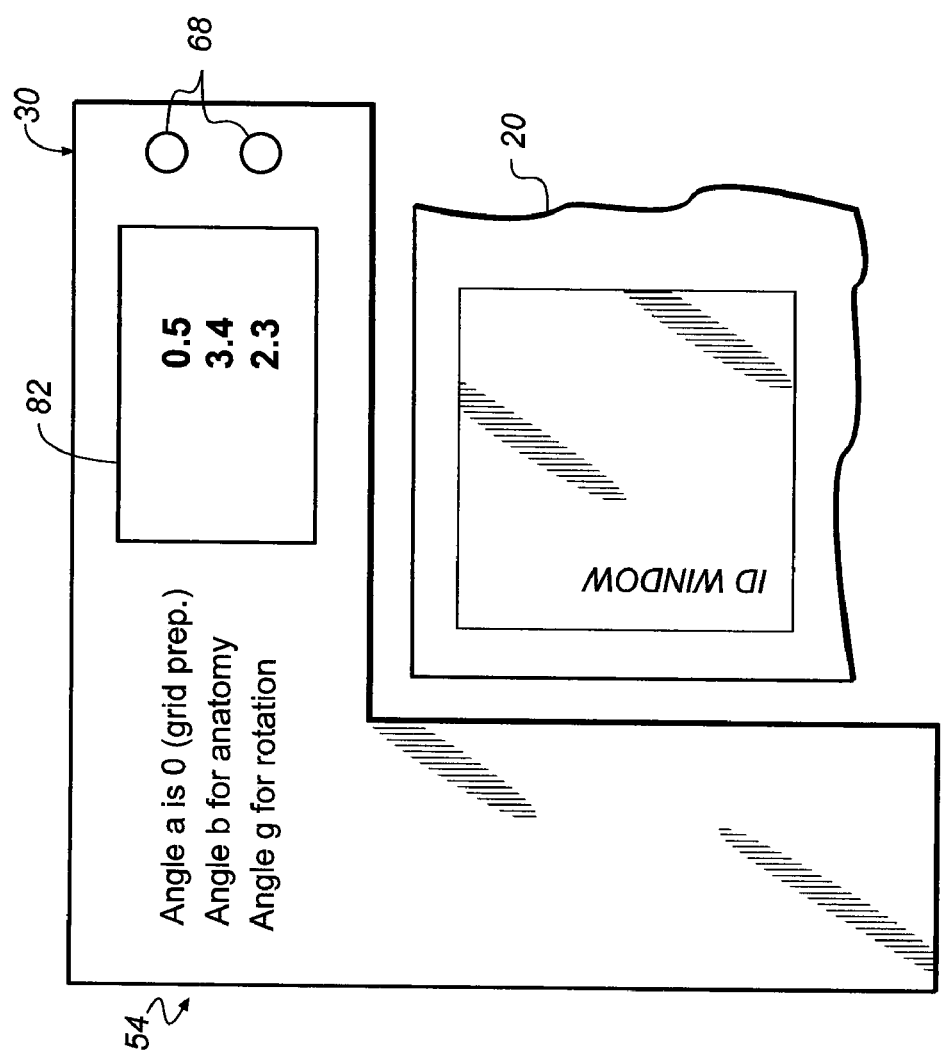
FIG. 19 is a view of the sensor of the present invention in an alternate embodiment having the display integrated as part of the sensor body.

The plan view of FIG. 19 shows an embodiment of display 54 having additional capabilities. Here, a numerical or text display portion 82 is provided, with variable text fields for listing data values themselves, possibly along with relevant information for the technician such as showing how to interpret the various data fields that are given.

Figure 22:
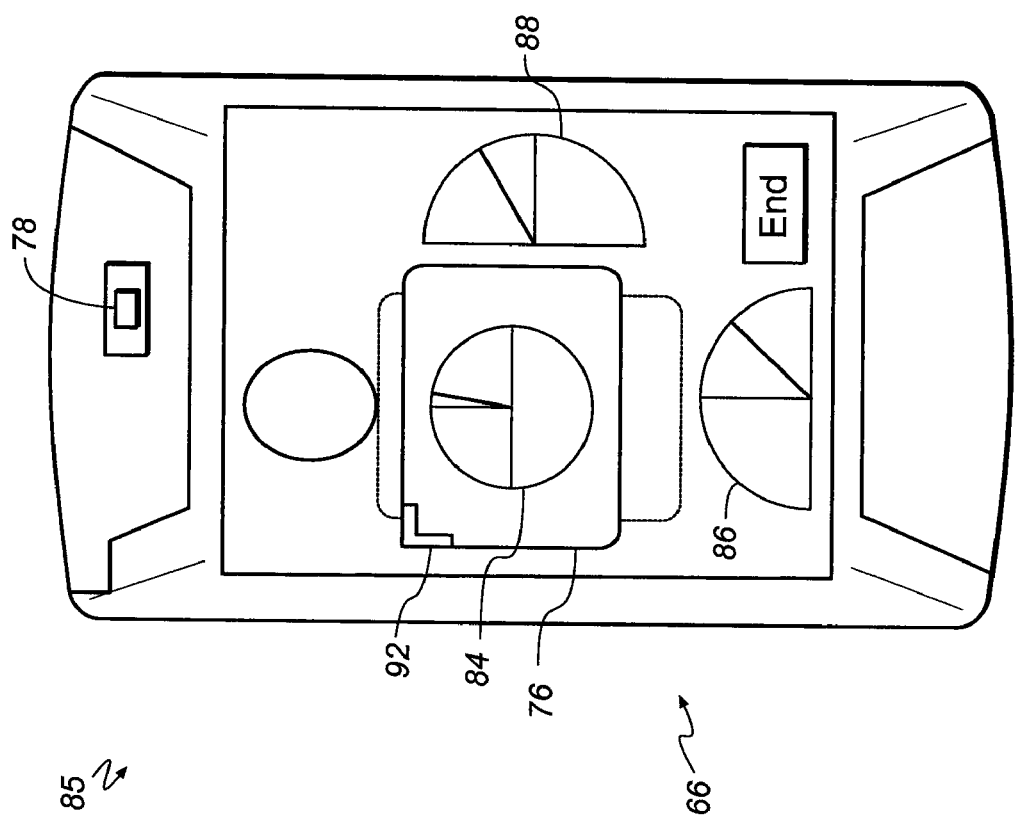
FIG. 22 shows a display monitor screen arranged for use with the sensor of the present invention, with display dials indicating angular orientations at a point in time.

FIG. 22 shows positional displays 66 as they might appear on an technician device that is separate from sensor apparatus 30, such as a wireless device, that acts as a control console 85. In the particular embodiment shown, a display dial 84 indicates rotation about the z axis. Another display dial 86 indicates rotation about the y axis (transformed to $\alpha$ in FIG. 4A), such as viewed from the feet of the patient. Similarly, another display dial 88 indicates rotation about the x axis (transformed to $\beta$ in FIG. 4B), such as viewed from the left side of the patient. An orientation icon 76 shows the basic layout of the cassette for imaging, whether landscape or portrait, with an icon 92 for sensor apparatus 30 visible on one corner. A reset switch 78 allows the technician to control console 85 to initiate zeroing of sensor apparatus 30 in a remote manner. This would be advantageous, for example, where sensor apparatus 30 is difficult to access in its position behind the patient.

Figure 20:
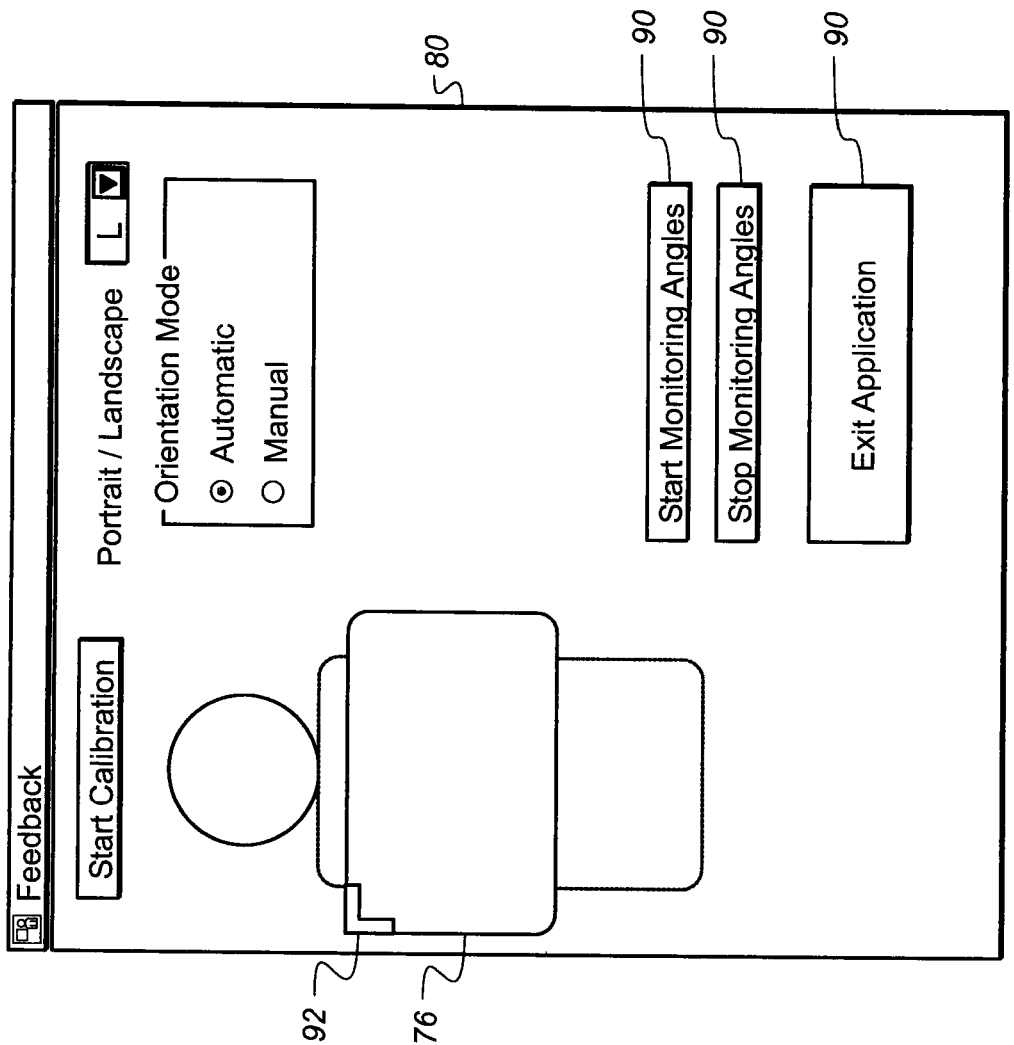
FIG. 20 shows a display monitor screen arranged for use with the sensor of the present invention, in a landscape orientation.
Figure 21:
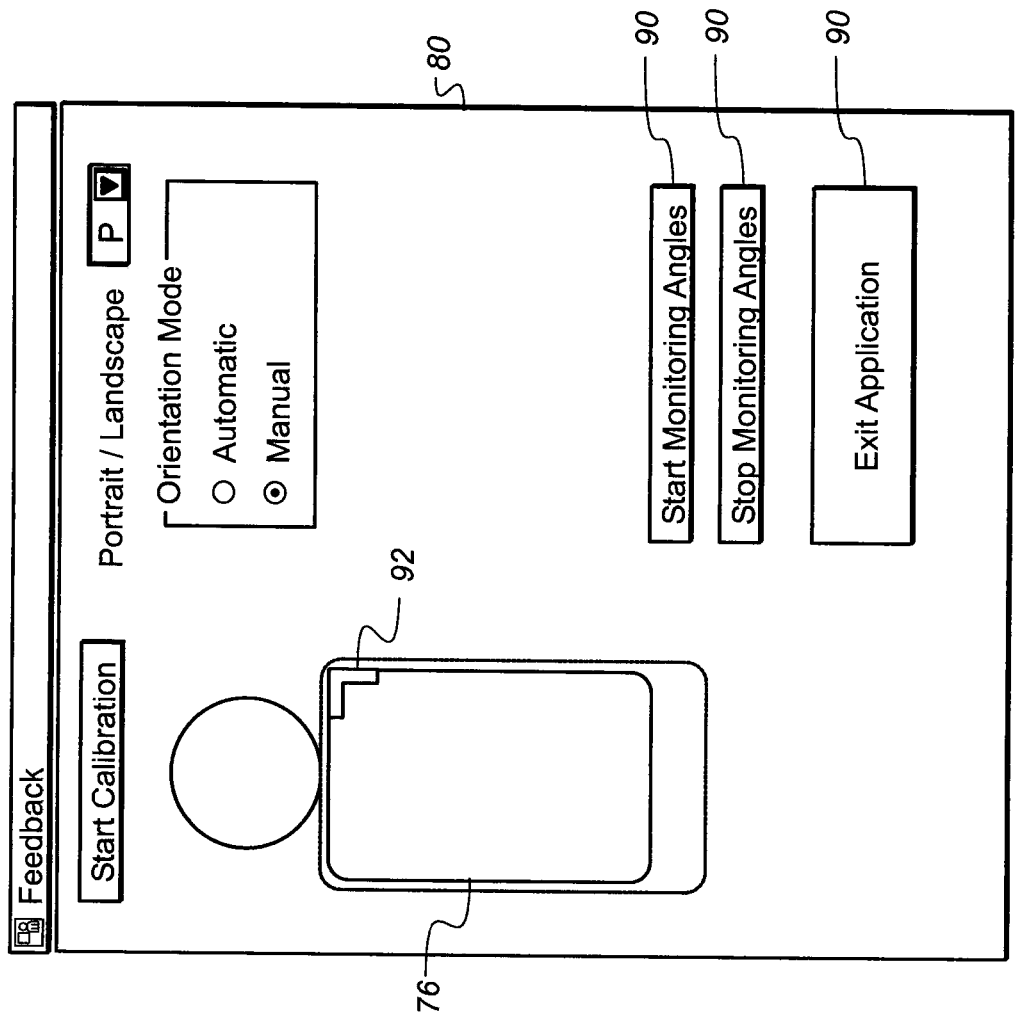
FIG. 21 shows a display monitor screen arranged for use with the sensor of the present invention, in a portrait orientation.

A conventional computer monitor can alternately be used for display 54. Referring to FIGS. 20 and 21, there are shown example displays that might appear on a touchscreen display 80. Command entry controls 90 would be buttons displayed on touchscreen display 80 and would allow the technician to initiate calibration and interactively view motion changes as sensor apparatus 30 is positioned. Icon 76 can be oriented on-screen as it is positioned behind the patient and may additionally show the position of sensor apparatus 30, as is indicated by a sensor icon 92 in FIGS. 20 and 21.

Sensor apparatus 30 does not yield a stable tilt or angular value, but provides constantly updated angular rate and acceleration data, which must be integrated in order to obtain accurate positional information. As noted earlier, there are a number of possible configurations of control processing logic for executing this task, with numerous ways of communicating the measurement data between sensor module 40 and the control logic processor.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, any of a number of different methods could be used for coupling sensor 30 to cassette 20 or to radiation head 12. For example, some type of fastener could be used, including clips, thumbscrews, brackets, screws, or other fastener devices. Thus, what is provided is an apparatus and method for providing proper alignment of the radiation source relative to an image detection device for recording a radiation image.

PARTS LIST

- 10 Portable radiation imaging apparatus
- 12 Radiation head
- 14 Radiation source
- 18, 18a Target
- 20 Cassette
- 22 Antiscatter grid
- 24 Lead strips
- 26 Focal spot
- 28 Focal line
- 30, 30a, 30b Sensor apparatus, inertial
- 31a, 31b Tilt sensors
- 32 Computer workstation
- 34 Display
- 36 Housing
- 37 Orientation sphere
- 38 Tab
- 40 Sensor module
- 41 Circle of uncertainty
- 42 Magnet
- 43, 45 Position of radiation head 12
- 46 Switch
- 48 Power supply
- 50 Indicator
- 52 Communications circuit
- 54 Display
- 56 Storage
- 58 Control logic processor
- 60 Technician interface
- 62 Power supply
- 66 Orientation display
- 68 Operational indicator
- 76 Cassette icon
- 80 Display
- 82 Text display portion
- 84, 86, 88 Display dial
- 85 Console
- 90 Controls
- 92 Sensor icon
- 100 Sensor setup step
- 110 Reset step
- 120 Sensor repositioning step
- 130 Feedback review step
- 140 Decision step
- 150 Head reorienting or repositioning step
- 160 Image capture step
- 200 Base calibration step
- 210 Patient side setup step
- 220. Initial head position step
- 230 Decision step
- 240 Readjustment step
- 250 Image capture step
- N. Normal to cassette 20
- O. Central axis of x-ray radiation
- $\alpha, \beta, \gamma$. Angle

The invention claimed is:

1. A radiation imaging system comprising:
   a radiation head including a radiation source and having an adjustable position and an adjustable angular orientation;
   a radiation image detection device comprising a photo-stimulable medium for recording an image according to radiation emitted from the radiation source;
   a single measurement sensor apparatus including a housing, the housing being adapted to be sequentially coupled first to the detection device and second to the radiation head, the measurement sensor apparatus continuously providing three-dimensional data for continuously determining changes in angular orientation of the measurement sensor apparatus while the measurement sensor apparatus
- (i) is coupled to the detection device,
- (ii) is being moved from a benchmark position in which the measurement sensor apparatus is coupled to the detection device to a position in which the measurement sensor apparatus is coupled to the radiation head, and
- (iii) is coupled to the radiation head;

a processor responsive to the three-dimensional data from the measurement sensor apparatus to continuously determine change in three-dimensional angular orientation of the single measurement sensor apparatus, whereby the change in three-dimensional angular orientation for use by an operator of the radiation imaging system to manually adjust angular orientation of the radiation head in at least one direction to align the radiation head to the image detection device; and at least one indicator responsive to the processor to continuously indicate to the operator at least one angular orientation adjustment of the radiation head to be made manually by the operator in at least one direction to align the radiation head to the image detection device.

2. The radiation imaging system of claim 1, wherein the detection device is encased in a cassette and the housing is detachable from the cassette.

3. The radiation imaging system of claim 2, wherein the housing comprises a magnetic coupling for engaging the cassette.

4. The radiation imaging system of claim 2, wherein the housing has paired tabs for maintaining a pressure fit against the cassette.

5. The radiation imaging system of claim 1, wherein the housing is detachable from the radiation head.

6. The radiation imaging system of claim 5, wherein the housing comprises a magnetic coupling for engaging the radiation head.

7. The radiation imaging system of claim 5, wherein the housing has paired tabs for maintaining a pressure fit against the radiation head.

8. The radiation imaging system of claim 1, wherein the detection device is encased in a cassette and the housing is detachable from the cassette and the radiation head.

9. The radiation imaging system of claim 8, wherein the housing comprises a magnetic coupling for engaging the cassette or the radiation head.

10. The radiation imaging system of claim 8, wherein the housing has paired tabs for maintaining a pressure fit against the cassette or the radiation head.

11. An apparatus for use to retrofit an existing radiation imaging system of a type including a radiation head and a radiation image detection device, the apparatus comprising:
- a housing, the housing being adapted to be sequentially coupled first to the detection device and second to the radiation head;
- a measurement sensor in the housing for continuously providing three-dimensional data for continuously determining changes in angular orientation of the housing while the housing
  - (i) is coupled to the detection device,
  - (ii) is being moved from a benchmark position in which the housing is coupled to the detection device to a position in which the housing is coupled to the radiation head, and
  - (iii) is coupled to the radiation head; and
- a processor responsive to the three-dimensional data from the measurement sensor to continuously determine a change in three-dimensional angular orientation of the housing, whereby the change in three-dimensional angular orientation for use by an operator of the existing radiation imaging system to manually adjust angular orientation of the radiation head in at least one direction to align the radiation head to the image detection device.

12. The measurement sensor apparatus of claim 11, further comprising at least one indicator in the housing responsive to the processor to continuously indicate to the operator at least one angular orientation adjustment of the radiation head to be made manually by the operator in at least one direction.

13. The measurement sensor apparatus of claim 11, wherein the detection device is encased in a cassette and the housing is detachable from the cassette.

14. The measurement sensor apparatus of claim 13, wherein the housing comprises a magnetic coupling for engaging the cassette.

15. The measurement sensor apparatus of claim 13, wherein the housing has paired tabs for maintaining a pressure fit against the cassette.

16. The measurement sensor apparatus of claim 11 wherein the housing is detachable from the radiation head.

17. The measurement sensor apparatus of claim 16, wherein the housing comprises a magnetic coupling for engaging the radiation head.

18. The measurement sensor apparatus of claim 16, wherein the housing has paired tabs for maintaining a pressure fit against the radiation head.

19. The measurement sensor apparatus of claim 11, wherein the detection device is encased in a cassette and the housing is detachable from the cassette and the radiation head.

20. The measurement sensor apparatus of claim 19, wherein the housing comprises a magnetic coupling for engaging the cassette or the radiation head.

21. The measurement sensor apparatus of claim 19, wherein the housing has paired tabs for maintaining a pressure fit against the cassette or the radiation head.

22. A method for obtaining a radiation image, using a radiation imaging system including a radiation head having a radiation source, a radiation aiming light for projecting a target onto a patient to be imaged and a radiation image detection device having a photostimulable medium for recording images according to radiation emitted from the radiation head, the method comprising steps of:
- providing a single measurement sensor apparatus, the measurement sensor apparatus comprising a housing, the housing being adapted to be sequentially coupled first to the radiation image detection device and second to the radiation head, the measurement sensor apparatus continuously providing three-dimensional data for continuously determining changes in angular orientation of the measurement sensor apparatus while the measurement sensor apparatus
  - (i) is coupled to the detection device,
  - (ii) is being moved from a benchmark position in which the measurement sensor apparatus is coupled to the detection device to a position in which the measurement sensor apparatus is coupled to the radiation head, and
  - (iii) is coupled to the radiation head;
- first coupling the measurement sensor apparatus to the detection device;

establishing a first set of benchmark three-dimensional data from the measurement sensor apparatus as coupled to the detection device;

while the sensor apparatus continuously provides the three-dimensional data, removing the measurement sensor apparatus from the detection device and second coupling the measurement sensor apparatus to the radiation head;

establishing a second set of three-dimensional data from the measurement sensor apparatus as coupled to the radiation head;

using a processor responsive to the sets of data from the measurement sensor apparatus, continuously determining changes in three-dimensional angular orientation of the measurement sensor apparatus, whereby the change in three-dimensional angular orientation for use by an operator of the radiation imaging system to manually adjust angular orientation of the radiation head in at least one direction;

indicating to the operator at least one angular orientation adjustment of the radiation head to be made manually by the operator in at least one direction;

projecting the target onto the patient; and with the measurement sensor apparatus coupled to the radiation head, manually adjusting the angular orientation of the radiation head according to the angular orientation adjustment to align the radiation head to the image detection device, while manually maintaining the target in a desired location on the patient.

* * * * *